(12) United States Patent
Beck

(10) Patent No.: US 9,877,879 B2
(45) Date of Patent: Jan. 30, 2018

(54) WASHABLE DIAPER

(71) Applicant: Sandra C. Beck, Rensselaer, NY (US)

(72) Inventor: Sandra C. Beck, Rensselaer, NY (US)

( * ) Notice: Subject to any disclaimer, the term of this patent is extended or adjusted under 35 U.S.C. 154(b) by 0 days.

(21) Appl. No.: 14/551,757

(22) Filed: Nov. 24, 2014

(65) Prior Publication Data

US 2015/0088086 A1  Mar. 26, 2015

Related U.S. Application Data

(63) Continuation of application No. 13/540,163, filed on Jul. 2, 2012, now Pat. No. 8,894,626.

(51) Int. Cl.
| | |
|---|---|
| *A61F 13/494* | (2006.01) |
| *A61F 13/49* | (2006.01) |
| *A61F 13/15* | (2006.01) |
| *A61F 13/505* | (2006.01) |
| *A61F 13/531* | (2006.01) |

(52) U.S. Cl.
CPC .. *A61F 13/49003* (2013.01); *A61F 13/15268* (2013.01); *A61F 13/494* (2013.01); *A61F 13/4906* (2013.01); *A61F 13/505* (2013.01); *A61F 13/15211* (2013.01); *A61F 13/15252* (2013.01); *A61F 2013/15276* (2013.01); *A61F 2013/5315* (2013.01)

(58) Field of Classification Search
CPC .......... A61F 2013/15276; A61F 13/505; A61F 13/494; A61F 13/49; A61F 13/15; A61F 13/15268; A61F 13/49003
See application file for complete search history.

(56) References Cited

U.S. PATENT DOCUMENTS

| | | | | |
|---|---|---|---|---|
| 4,397,646 A | * | 8/1983 | Daniels | ............. A61F 13/49004 604/381 |
| 4,872,871 A | * | 10/1989 | Proxmire | .......... A61F 13/49007 604/385.22 |
| 5,185,011 A | * | 2/1993 | Strasser | ............ A61F 13/49004 604/385.15 |

* cited by examiner

*Primary Examiner* — Tatyana Zalukaeva
*Assistant Examiner* — Sara Sass
(74) *Attorney, Agent, or Firm* — Heslin Rothenberg Farley & Mesiti, P.C.; Kristian E. Ziegler, Esq.

(57) ABSTRACT

A washable diaper having an outer article and an inner liner system detachably coupled to the outer article is disclosed. The inner liner system may include front and back ends and a liner member about a washable article with an absorbent pad positioned therein. The outer article may include front and back ends with opposing side edges extending therebetween. The outer article may include an inner surface with substantially liquid impervious compartments at the front and back ends. The outer article and the inner article may include fastening mechanisms configured to removably couple the inner liner system to the outer article such that at least the front and back ends of the washable article of the inner liner system are substantially secured within the front and back liquid impervious pockets, respectively, when the outer article and inner liner system are assembled.

13 Claims, 20 Drawing Sheets

WASHABLE DIAPER

CROSS-REFERENCE TO RELATED APPLICATION

This application is a continuation of U.S. patent application Ser. No. 13/540,163, filed Jul. 2, 2012, which is a continuation-in-part of U.S. patent application Ser. No. 12/469,357, filed May 20, 2009, the disclosures of which are hereby expressively incorporated herein by reference in their entirety.

FIELD OF INVENTION

The invention relates generally to diapers. More particularly, the present invention relates to washable and reusable diapers.

BACKGROUND INFORMATION

Disposable diapers and cloth diapers for the absorption and containment of urine and other bodily excrements are generally known in the art. Disposable diapers have been convenient, but are costly and present environmentally adverse consequences.

Cloth diapers with flushable components have been developed, but continue to be inconvenient, bulky, and present unsanitary conditions because of inadequate construction of the diaper. Cloth diapers are often used in conjunction with waterproof plastic pants to provide some protection against leakage. Unfortunately, adding this additional element does not generally solve the longstanding waste constraint and disposal difficulties.

BRIEF SUMMARY OF THE INVENTION

The present invention provides a solution to these identified problems. The present invention provides a durable washable diaper with the convenience and effectiveness of a traditional disposable diaper without the adverse environmental consequences. Consumers will save money and reduce consumer waste because the washable diaper and the absorbent articles are reusable. The liquid pervious liner of the inner liner system, captures any non-liquid waste, and is easily removable in its entirety and disposed through a regular toilet. The option of the immediate disposal of solid bodily waste provides increased sanitary conditions.

The present invention provides in one aspect a washable diaper that includes an outer article, and an inner liner system. In some such embodiments, the outer article is configured with a first end including a first substantially liquid impervious compartment, a second end including a second substantially liquid impervious compartment and a medial portion with opposing side edges extending between the first and second ends thereof. In some such embodiments the outer article further comprises an inner surface and an outer surface. In some such embodiments, the inner liner system comprises at least one washable article having a first end and a second end. In some such embodiments, when the inner liner system is assembled with the outer article, the inner liner system is detachably coupled to the outer article and adjacent the inner surface thereof, the first end of at least the at least one washable article of the inner liner system is positioned within the first compartment of the outer article, and at least the second end of the at least one washable article of the inner liner system is positioned within the second compartment of the outer article.

In some embodiments the outer article defines a perimeter including the opposing side edges, and wherein at least a portion of the perimeter includes at least one substantially liquid impervious member secured thereto. In some such embodiments the substantially liquid impervious member is sewn over the perimeter of the outer article by substantially non-wicking thread. In some such embodiments, the substantially non-wicking thread is a polyester thread.

In some embodiments the outer article defines a medial portion extending between the first and second substantially liquid impervious compartments. In some such embodiments, the first and second compartments are positioned on an inner surface of the outer article and include an opening accessible from the medial portion of the outer article. In some such embodiments, the outer article includes a substantially liquid impervious material, and the first and second compartments of the outer article are formed at least in part from the outer article being folded over upon itself such that the inner surface of the outer article forms opposing interior surfaces of the first and second substantially liquid impervious compartments. In some such embodiments, the outer article defines a perimeter, and at least a portion of the perimeter of the outer article includes at least one substantially liquid impervious member secured thereover via substantially non-wicking thread. In some such embodiments, the at least one substantially liquid impervious member and substantially non-wicking thread forms substantially liquid impervious opposing sides edges of the first and second substantially liquid impervious compartments.

In some embodiments, the washable diaper further comprises at least one fastening mechanism for detachably coupling the inner liner system to the outer article such that the first end of the inner liner system is selectively secured within the first substantially liquid impervious compartment of the outer article and the second end of the inner liner system is selectively secured within the second substantially liquid impervious compartment of the outer article. In some embodiments, the at least one fastening mechanism includes a first fastening mechanism comprising a first component associated with the outer article and a second component for mating with the first component associated with the at least one washable article for detachably coupling the inner liner system to the outer article such that the first end of at least the at least one washable article is selectively secured within the first substantially liquid impervious compartment of the outer article. In some such embodiments, the at least one fastening mechanism further includes a second fastening mechanism comprising a third component associated with the outer article and a fourth component for mating with the third component associated with the at least one washable article for detachably coupling the inner liner system to the outer article such that the second end of at least the at least one washable article is selectively secured within the second substantially liquid impervious compartment of the outer article. In some such embodiments, the inner liner system further comprises a liner member fabricated from a substantially liquid pervious biodegradable material, and the at least one fastening mechanism detachably couples the liner member to the outer article and the at least one washable article such that at least a portion of the liner member substantially covers at least a portion of an inner surface of the at least one washable article when the inner liner system is assembled with the outer article.

In some embodiments, the at least one washable article includes an internal cavity with an opening, and the inner liner system further comprises at least one absorbent pad removably secured within the internal cavity. In some such embodiments, the opening of the at least one washable article and the at least one absorbent pad are configured such that the opening defines a length that is greater than the largest length of the at least one absorbent pad. In some such embodiments, the at least one washable article includes fastening mechanisms configured to bias the opening in an open position when the fastening mechanism are fastened. In some such embodiments, the longitudinal length of the opening is at least about 80% of the longitudinal length of the at least one absorbent pad.

In some embodiments, a portion of the medial portion of the outer article comprises side barrier assemblies at the opposing side edges. In some such embodiments, each side barrier assembly comprises a substantially liquid impervious barrier panel with a generally semicircle shape including a substantially curved edge and a substantially linear edge.

In some such embodiments, each side barrier assembly further comprises substantially liquid impervious banding secured over the substantially curved edge of the corresponding barrier panel and the corresponding side edge of the outer article with substantially non-wicking thread such that the barrier panel and the outer article are coupled to one another, form a substantially liquid impervious seal therebetween, and the corresponding barrier panel is biased in a direction extending substantially away from the inner surface of the outer article. In some such embodiments, each side barrier assembly further comprises an elasticized member coupled to the substantially linear edge of the corresponding barrier panel such that the elasticized member biases at least the inner surface of the medial portion of the outer article into a generally convex shape.

In some embodiments, the outer article includes a generally pocket-shaped member removably attached to the outer surface thereof proximate to the second end.

In some embodiments, the outer article further comprises side barriers, the side barriers extending from the inner surface and oriented substantially parallel to each other, and the inner liner system is positioned fully between the side barriers to inhibit movement thereof when the inner liner system is assembled with the outer article.

In accordance with another aspect, a method of assembling a washable diaper is disclosed. In some embodiments, the method of assembling a washable diaper comprises obtaining a reusable outer article, obtaining at least one washable article, and detachably coupling the at least one washable article to the reusable outer article. In some such embodiments, the reusable outer article has a front end, a back end, a medial portion with opposing side edges extending between the front and back ends thereof, an outer surface and an inner surface. In some such embodiments, the inner surface includes a first substantially liquid impervious compartment positioned at the front end of the reusable outer article and a second substantially liquid impervious compartment positioned at the back end of the reusable outer article. In some such embodiments, the at least one washable article has a first and second end and inner and outer surfaces. In some such embodiments, the method includes positioning the first end of the at least one washable article within the first substantially liquid impervious compartment of the reusable outer article and the second end of the at least one washable article within the second substantially liquid impervious compartment of the reusable outer article.

In some embodiments, the first and second substantially liquid impervious compartments include an opening accessible from the medial portion of the reusable outer article. In some such embodiments, the outer article comprises a substantially liquid impervious material. In some such embodiments, each of the first and second compartments of the outer article are formed at least in part from the substantially liquid impervious material of the outer article.

In some embodiments, each of the first and second compartments of the outer article are formed at least in part by the substantially liquid impervious material of the outer article being folder over upon itself. In some such embodiments, outer edges of the outer article include at least one substantially liquid impervious member secured thereover via substantially non-wicking thread, and the at least one substantially liquid impervious member and thread forms opposing substantially liquid impervious sides of the first and second compartments.

In some embodiments, the outer article and the at least one washable article include mating fastening mechanisms for detachably coupling the at least one washable article to the reusable outer article such that at least the first end of the at least one washable article is selectively secured within the first substantially liquid impervious compartment of the reusable outer article and at least the second end of the at least one washable article is selectively secured within the second substantially liquid impervious compartment of the reusable outer article when the fastening mechanisms are coupled to one another. In some such embodiments, the step of detachably coupling the at least one washable article to the reusable outer article includes fastening the mating fastening mechanisms to one another.

In some embodiments, the method further comprising the steps of obtaining a liner member fabricated from a substantially liquid pervious biodegradable material, substantially covering at least a portion of the inner surface of the at least one washable article with the liner member, and detachably coupling the liner member to the at least one washable article and the reusable outer article. In some such embodiments, the steps of detachably coupling the liner member to the at least one washable article and the reusable outer article, and detachably coupling the at least one washable article to the reusable outer article are accomplished at least in part by coupling mating fastening mechanisms associated with the at least one washable article and the reusable outer article to one another.

In some embodiments, the method further includes the steps of obtaining at least one absorbent pad, removably positioning the at least one absorbent pad within a cavity in the at least one washable article through an opening in the at least one washable article, and unfastening fastening members provided on the one washable article and thereby biasing the opening of the washable article in an open position to bias the opening in a closed position.

In accordance with another aspect, a method of manufacturing a washable diaper is disclosed. In some such embodiments, the method includes the step of manufacturing an outer article of the washable diaper. In some such embodiments, the method of manufacturing an outer article of the washable diaper includes the step of forming a first substantially liquid impervious portion of a shape that includes a front end, a back end, a medial portion with opposing side edges extending between the front and back ends, an outer surface and an inner surface. In some such embodiments, the method of manufacturing an outer article of the washable diaper further includes the step of folding a first compartment portion of the first substantially liquid impervious portion that is adjacent the front end towards the back end thereof such that the inner surfaces of the first compartment portion and the adjacent portion of the first substantially liquid impervious portion form a first compartment with a substantially liquid impervious bottom edge and an opening accessible from the medial portion of the first substantially liquid impervious portion. In some such embodiments, the method of manufacturing an outer article of the washable diaper further includes the step of coupling at least one second substantially liquid impervious portion over at least the side edges of the first compartment such that the side edges of the first compartment are substantially liquid impervious. In some such embodiments, the method of manufacturing an outer article of the washable diaper further includes the step of folding a second compartment portion of the first substantially liquid impervious portion that is adjacent the back end towards the front end such that the inner surfaces of the second compartment portion and the adjacent portion of the first substantially liquid impervious portion form a second compartment with an opening accessible from the medial portion of the first substantially liquid impervious portion. In some such embodiments, the method of manufacturing an outer article of the washable diaper further includes the step of coupling at least one third substantially liquid impervious portion over at least the side edges of the second compartment such that the side edges of the second compartment are substantially liquid impervious.

In some embodiments, forming the first substantially liquid impervious portion includes cutting the first substantially liquid impervious portion out from substantially liquid impervious material. In some such embodiments, cutting the first substantially liquid impervious portion out from substantially liquid impervious material includes utilizing a template in the shape of the first substantially liquid impervious portion.

In some embodiments, the at least one second and third substantially liquid impervious portions are portions of substantially liquid impervious banding, and wherein coupling the second and third substantially liquid impervious portions over the opposing side edges of the first and second compartments, respectively, includes stitching the substantially liquid impervious banding thereto with substantially non-wicking thread. In some such embodiments, the sewing of the substantially liquid impervious banding over the side edges of the first and second compartments, respectively, with substantially non-wicking thread includes sewing the substantially liquid impervious banding over the side edges of the first and second compartments, respectively. In some such embodiments, the sewing the substantially liquid impervious banding over the side edges of the first and second compartments, respectively, includes sewing with polyester thread via a ball needle. In some other such embodiments, the sewing of the substantially liquid impervious banding portions over the side edges of the first compartment includes passing the substantially non-wicking thread at least through the substantially liquid impervious banding portions a first time, the first compartment portion of the first substantially liquid impervious portion, the portion of the first substantially liquid impervious portion adjacent the first compartment portion forming the first compartment, and the substantially liquid impervious portions a second time, and wherein the sewing of the substantially liquid impervious banding portions over the side edges of the second compartment includes passing the substantially non-wicking thread at least through the substantially liquid impervious banding portions a first time, the second compartment portion of the first substantially liquid impervious portion, the portion of the first substantially liquid impervious portion adjacent the second compartment portion forming the second compartment, and the substantially liquid impervious substantially impervious material a second time.

In some embodiments, manufacturing an outer article of the washable diaper further comprises manufacturing side barrier assemblies on the medial portion of the first substantially liquid impervious portion at each opposing side edge thereof.

In some such embodiments, manufacturing the side barrier assemblies comprises forming second and third substantially liquid impervious portions of a generally semicircle shape including a substantially curved edge and a substantially linear edge. In some such embodiments, manufacturing the side barrier assemblies further comprises securing substantially liquid impervious banding over the substantially curved edge of the second substantially liquid impervious portion and one of the opposing side edges of the first substantially liquid impervious portion with substantially non-wicking thread such that the first and second portions are coupled to one another, form a substantially liquid impervious seal therebetween, and the second portion is biased in a direction extending substantially away from the inner surface of the first portion. In some such embodiments, manufacturing the side barrier assemblies further comprises securing substantially liquid impervious banding over the substantially curved edge of the third substantially liquid impervious portion and the other of the opposing side edges of the first substantially liquid impervious portion with substantially non-wicking thread such that the first and third portions are coupled to one another, form a substantially liquid impervious seal therebetween, and the third portion is biased in a direction extending substantially away from the inner surface of the first portion. In some such embodiments, manufacturing the side barrier assemblies further comprises securing an elasticized member to the substantially linear edge of each of the second and third substantially liquid impervious portions such that the elasticized members bias at least the inner surface of the first substantially liquid impervious portion into a generally convex shape.

In accordance with another aspect, an inner liner system for use with an outer article of a washable diaper is disclosed. In some such embodiments, the inner liner system comprises an elongate washable article defining a first longitudinal length greater than a first lateral width and including an internal cavity and a longitudinally extending opening in a medial portion of the first width in communication with the internal cavity that defines a second longitudinal length. In some such embodiments, the washable article is substantially liquid pervious and absorbent. In some such embodiments, the inner liner system further comprises an absorbent pad that is substantially liquid pervious and absorbent that defines a third longitudinal length. In some such embodiments, the absorbent pad and the internal cavity of the washable article are configured such that the absorbent pad can be carried within the cavity when the inner liner system is used with the outer article.

In some embodiments, the second longitudinal length of the opening of the washable article is at least about 80% of the third longitudinal length of the absorbent pad. In some embodiments, the at least one washable article includes fastening mechanisms configured to bias the opening in an open position when the fastening mechanism are fastened.

Other objects, aspects and advantages of the present invention, and/or of the currently preferred embodiments thereof, will become more readily apparent in view of the following detailed description of exemplary embodiments and the accompanying drawings.

BRIEF DESCRIPTION OF THE DRAWINGS

The subject matter, which is regarded as the invention, is particularly pointed out and distinctly claimed in the claims at the conclusion of the specification. The foregoing and other objects, features, and advantages of the invention are apparent from the following detailed description taken in conjunction with the accompanying drawings in which:

DETAILED DESCRIPTION

The following detailed description of a washable diaper illustrates by way of example and not by way of limitation. While the detailed description is made in the context of a diaper, it is apparent that the present invention would also be suitable for feminine care products, incontinence garments, training pants, and the like. Generally stated, disclosed herein is an embodiment of a washable diaper, comprising of an outer article and an inner liner system. Further described herein is a method of assembling an embodiment of the washable diaper.

Figure 1:
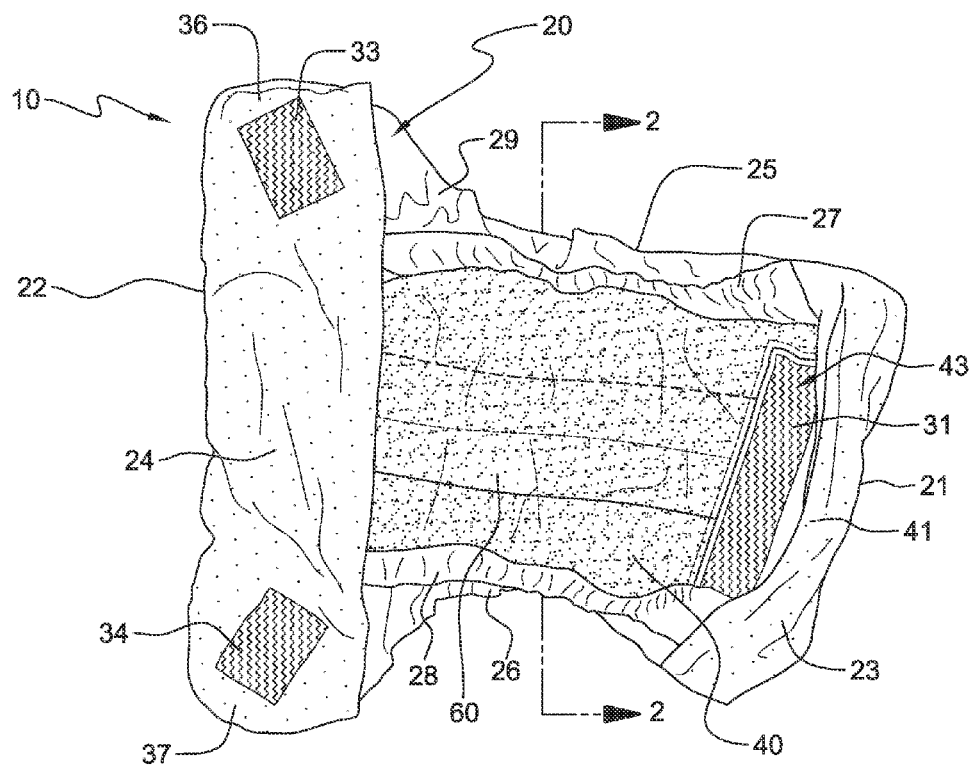
FIG. 1 is a top plan view of one embodiment of a washable diaper, showing an assembled inner liner system detachably coupled to an outer article, in accordance with an aspect of the present invention.

One embodiment of a washable diaper 10, embodying the principles and concepts of the present invention, is illustrated in FIGS. 1-9 and described below. FIG. 1 shows washable diaper 10 that has been assembled, comprising an outer article 20, and an inner liner system 40.

Figure 5:
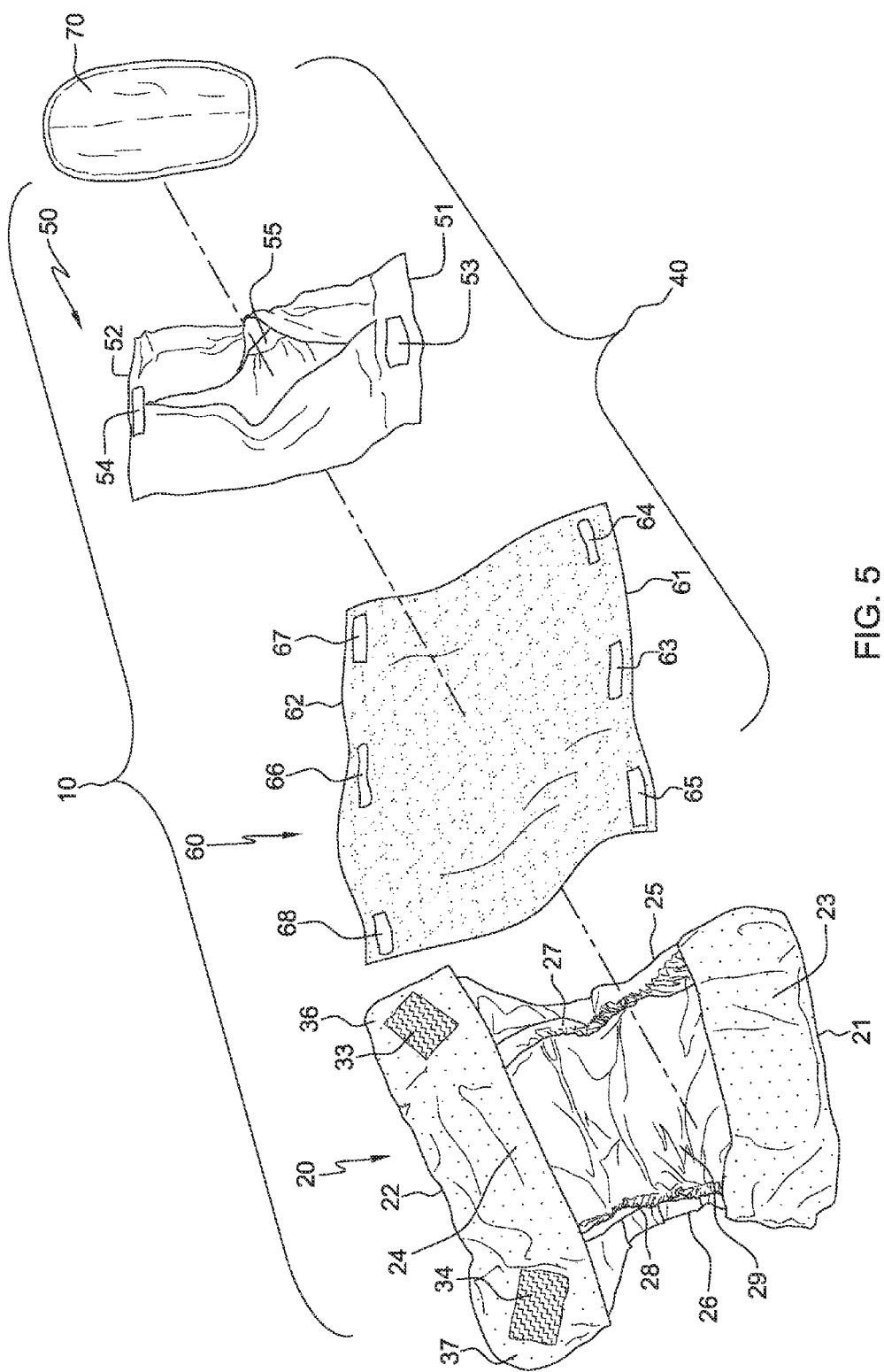
FIG. 5 is an exploded perspective view of the washable diaper of FIG. 1, showing the outer article, the inner liner system that includes a flushable liner, one washable article, and one absorbent pad, in accordance with an aspect of the present invention.

As illustrated in FIG. 5, one embodiment of washable diaper 10 may be assembled with at least one absorbent pad 70, at least one washable article 50, a liner member 60 and outer article 20. At least one absorbent pad 70 is fabricated from any absorbent material, including but not limited to, cotton, flannel, and organic cotton. At least one absorbent pad 70 may further be shaped to better suit the needs of male wearers or female wearers. In assembling washable diaper 10, at least one absorbent pad 70 is inserted within at least one washable article 50, through an opening 55 configured to accept at least one absorbent pad 70.

As seen in FIG. 5, at least one washable article 50 has a first end 51 and a second end 52, and also includes an opening 53 located about first end 51 and an opening 54 located about second end 52. Openings 53, 54 are located on opposing ends of at least one washable article 50. At least one washable article 50 further comprises opening 55 that is configured to receive at least one absorbent pad 70. Opening 55 is disposed on at least one washable article 50 and may be configured to extend longitudinally from first end 51 to second end 52 of washable article 50, and may be located in various positions, including on the front side, back side, or either lateral sides of at least one washable article 50, so long as opening 55 can accommodate the insertion of at least one absorbent pad 70. At least one washable article 50 is typically fabricated from any absorbent material, including, but not limited to, cotton, flannel, and organic cotton.

Figure 6A:
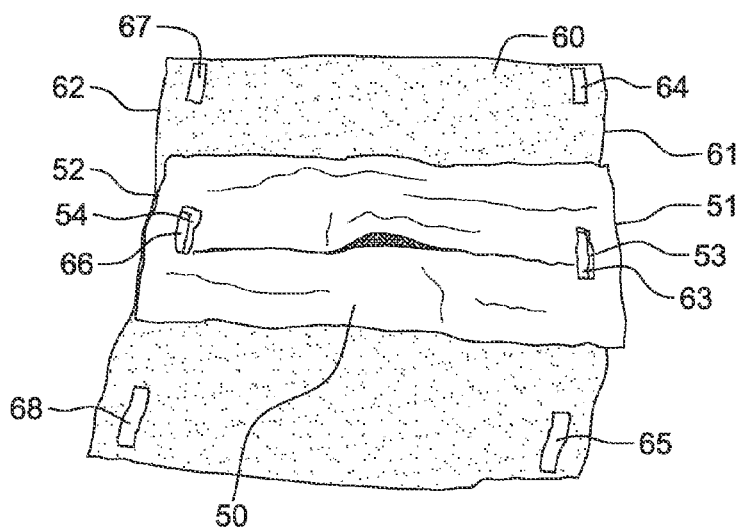
FIG. 6A is a top plan view of the inner liner system that includes the flushable liner and at least one washable article being aligned for assembly, in accordance with an aspect of the present invention.
Figure 6B:
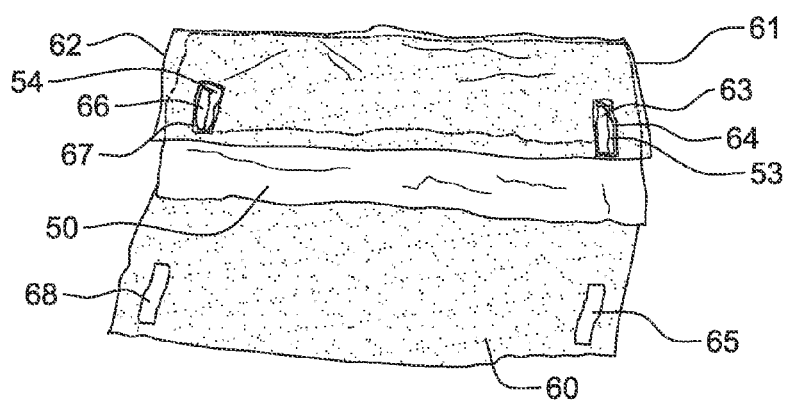
FIG. 6B is a top plan view of the flushable liner and at least one washable article, with one edge of the flushable liner folded over to cover the at least one washable article, in accordance with an aspect of the present invention.
Figure 6C:
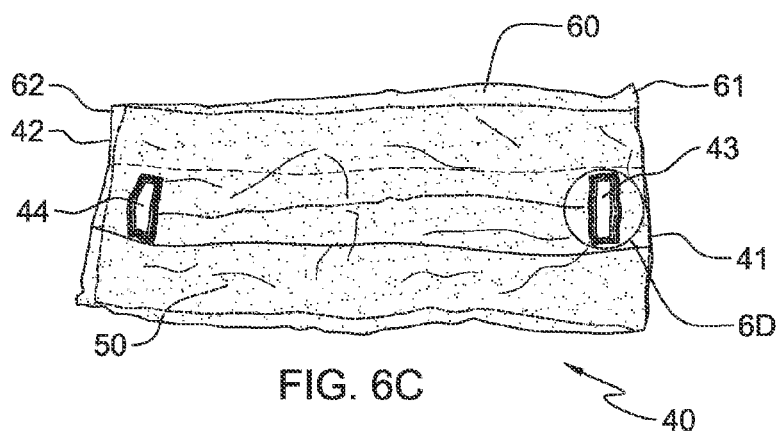
FIG. 6C is a top plan view of the assembled inner liner system that includes the flushable liner and at least one washable article, aligned for assembly with the outer article and with both edges of the flushable liner folded over to cover the at least one washable article, in accordance with an aspect of the present invention.

As exhibited in FIGS. 6A-6C, at least one washable article 50, that may have at least one absorbent pad 70 placed within, is wrapped by or enclosed within liner member 60. Liner member 60, having a first end 61 and a second end 62, has at least one opening 63 on first end 61 and at least one opening 66 on second end 62. Liner member 60 is compliant, soft feeling, and non-irritant to the wearer's skin. Liner member 60 may be fabricated from a liquid pervious material, including but not limited to, rice paper, cellulose fibers, blend of rayon and cellulose fibers and any other liquid permeable hydrophobic fibrous materials that will allow liquid to readily penetrate through its thickness. Liner member 60 may also be fabricated from a material that will wick moisture away from the wearer's skin. Liner member 60 may further still be fabricated from a material that is biodegradable and flushable through a regular toilet system. A person having ordinary skill in the art is aware of the type of liquid pervious material that can be used to manufacture liner member 60 so that it would be biodegradable and flushable. When liner member 60 is fabricated from a liquid pervious, flushable material, it will function to contain non-liquid bodily excrements and allow for easy disposal via a regular septic/sewer system.

Figure 6D:
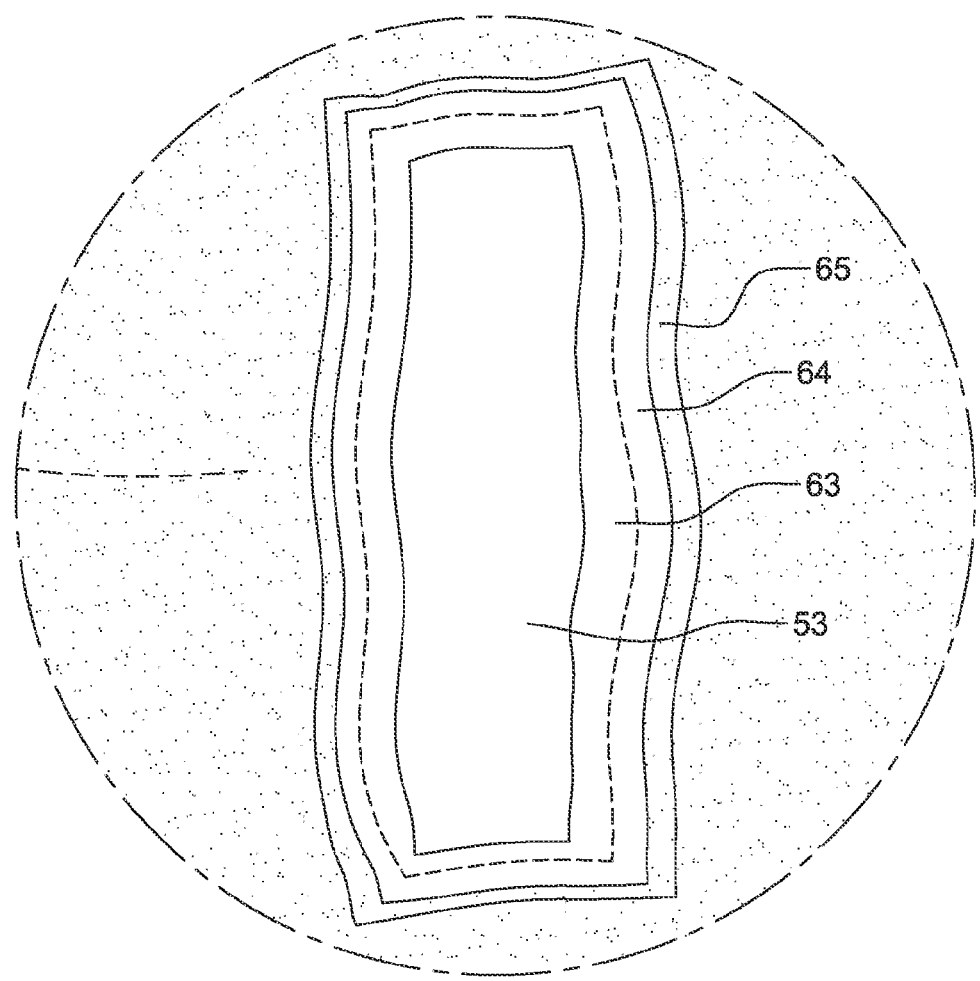
FIG. 6D is an enlarged top plan view, showing the opening at one end of the assembled inner liner system created by aligning the openings of the flushable liner and at least one washable article, in accordance with an aspect of the present invention.

As shown in FIG. 6A, liner member 60 has a length that is approximately the same as at least one washable article 50 and width that is generally wider than at least one washable article 50. Liner member 60 further has three openings 63, 64, 65 on first end 61 and three openings 66, 67, 68 on second end 62. As shown in FIG. 6C, assembled inner liner system 40 has an opening 43 at the first end 41 and an opening 44 at the second end 42. As shown in FIG. 6D, openings 63, 64, 65 on first end 61 of liner member 60 are coaxially aligned with opening 53 on first end 51 of at least one washable article 50 to form opening 43 (shown in FIG. 6C) at first end 41 inner liner system 40.

FIG. 5 shows inner liner system 40 being constructed of at least one absorbent pad 70 placed within at least one washable article 50 and liner member 60. Inner liner system 40 is then configured to detachably couple to outer article 20 by aligning inner liner system 40 adjacent to the inner surface 29 of outer article 20 and, by using the at least one fastening mechanism 31 disposed on the inner surface of the front end 21 (shown in FIG. 1) and the at least one fastening mechanism 32 disposed on the inner surface of the back end 22 (shown in FIG. 7) of outer article 20.

As seen in FIG. 1, first end 41 of inner liner system 40 is aligned with front end 21 and is positioned to be held within the front compartment 23 of outer article 20. Front compartment 23 is configured to receive first end 41 of inner liner system 40 and at least one fastening mechanism 31 detachably couples first end 41 of inner liner system 40 to outer article 20 by coupling opening 43. As also shown in FIG. 1, at least one fastening mechanism 31 is located on front end 21 and is disposed on the inner surface of front compartment 23 of outer article 20 and may be constructed by using hook and loop fasteners, such as the Velcro® brand hook and loop fastener system, but at least one fastening mechanism 31 may also be constructed by using a hook and eye, pin, button, snap button or clasp mechanisms.

Figure 7:
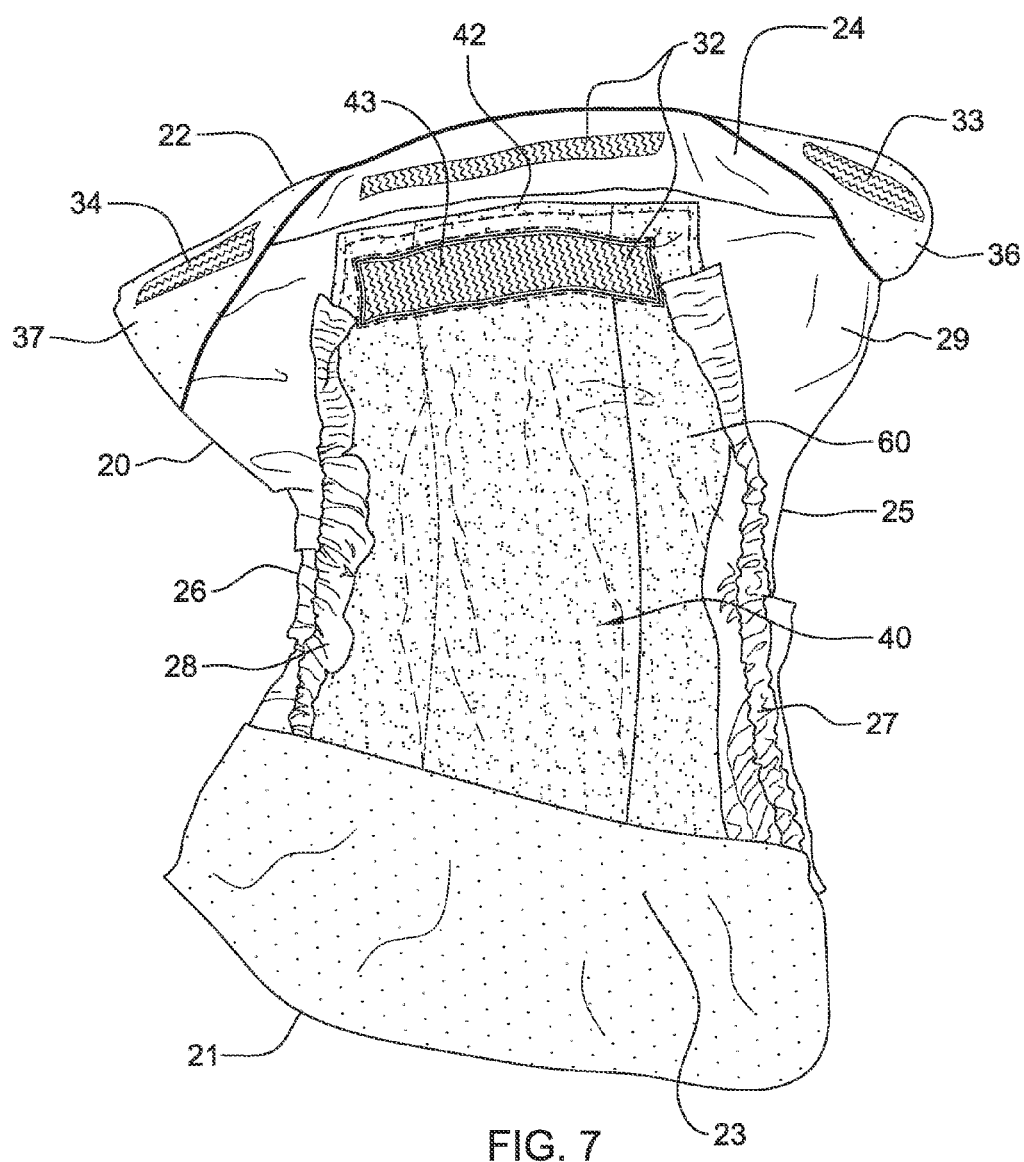
FIG. 7 is a perspective view of the washable diaper of FIG. 1, showing the inner surface of the back end of the outer article and the back compartment, illustrating the fastening mechanism detachably coupling one end of the inner liner system to the back end of the outer article, in accordance with an aspect of the present invention.

As shown in FIG. 7, second end 42 of inner liner system 40 is aligned with back end 22 and is positioned to be held within the back compartment 24 of outer article 20. Back compartment 24 is configured to receive second end 42 of inner liner system 40 and at least one fastening mechanism 32 detachably couples second end 42 of inner liner system 40 to outer article 20. As also exhibited in FIG. 7, at least one fastening mechanism 32 is disposed on the inner surface of back compartment 24 of outer article 20 and may be constructed using hook and loop fasteners, such as the Velcro® brand hook and loop fastener system, but at least one fastening mechanism 32 may also be constructed by using a hook and eye, pin, button, snap button or clasp mechanisms.

As illustrated in FIGS. 1, 5 and 7, outer article 20 is configured with front end 21 and back end 22, and the opposing side edges 25, 26. Outer article 20 may also include the opposing side barriers 27, 28, situated on inner surface 29 of outer article 20 and positioned substantially parallel to opposing side edges 25, 26. As shown in FIGS. 1, 2, 5, and 7, opposing side barriers 27, 28 may be elasticized.

FIGS. 1, 3, 4, 5 and 7 illustrate opposing side edges 25, 26 being configured to conform to the legs of the wearer to maximize fit and minimize potential leakage. This configuration gives outer article 20 an hourglass-like silhouette, with back end 22 being wider than front end 21 due to the extended portions 36, 37 of back end 22. Outer article 20 has back compartment 24, extending perpendicular to opposing sides edges 25, 26, that will allow extended portions 36, 37 to wrap around the wearer's body from the back side to the front side, as seen in FIG. 9. Outer article 20 also has front compartment 23, extending relatively perpendicular to opposing side edges 25, 26, that will allow wrapping around the wearer's body on the front side, as seen in FIG. 8.

In this embodiment of washable diaper 10, front compartment 23 and back compartment 24 are fashioned as a pocket or enclosure like structure, as illustrated in FIGS. 1, 3, 4, 5, and 7, but front compartment 23 and/or back compartment 24 may be designed as a flap, a pouch, reinforced patch of material or reinforced strip of material.

Outer article 20, as shown in FIGS. 1, 3, 4, 5, and 7-9, may be constructed using any material that will allow inner surface 29 (as shown in FIGS. 3, 4, 5 and 7) of outer article 20 to be liquid impervious. Outer article 20 may be comprised of a single layer shell construct manufactured from a liquid impervious material, or liquid resistant material, including but not limited to nylon. Outer article 20 may also be constructed using multiple layers of material, with one layer being constructed of a liquid impervious layer. When outer article 20 is made of multiple layers, a liquid impervious layer may be disposed as one of the inner layers. The outer-most layer may be manufactured from any material, including but not limited to a breathable material. The outer-most layer may also be manufactured from any material that would be desirable, including for the purpose of increasing the comfort for the wearer, and enhancing the aesthetics of washable diaper 10.

Figure 8:
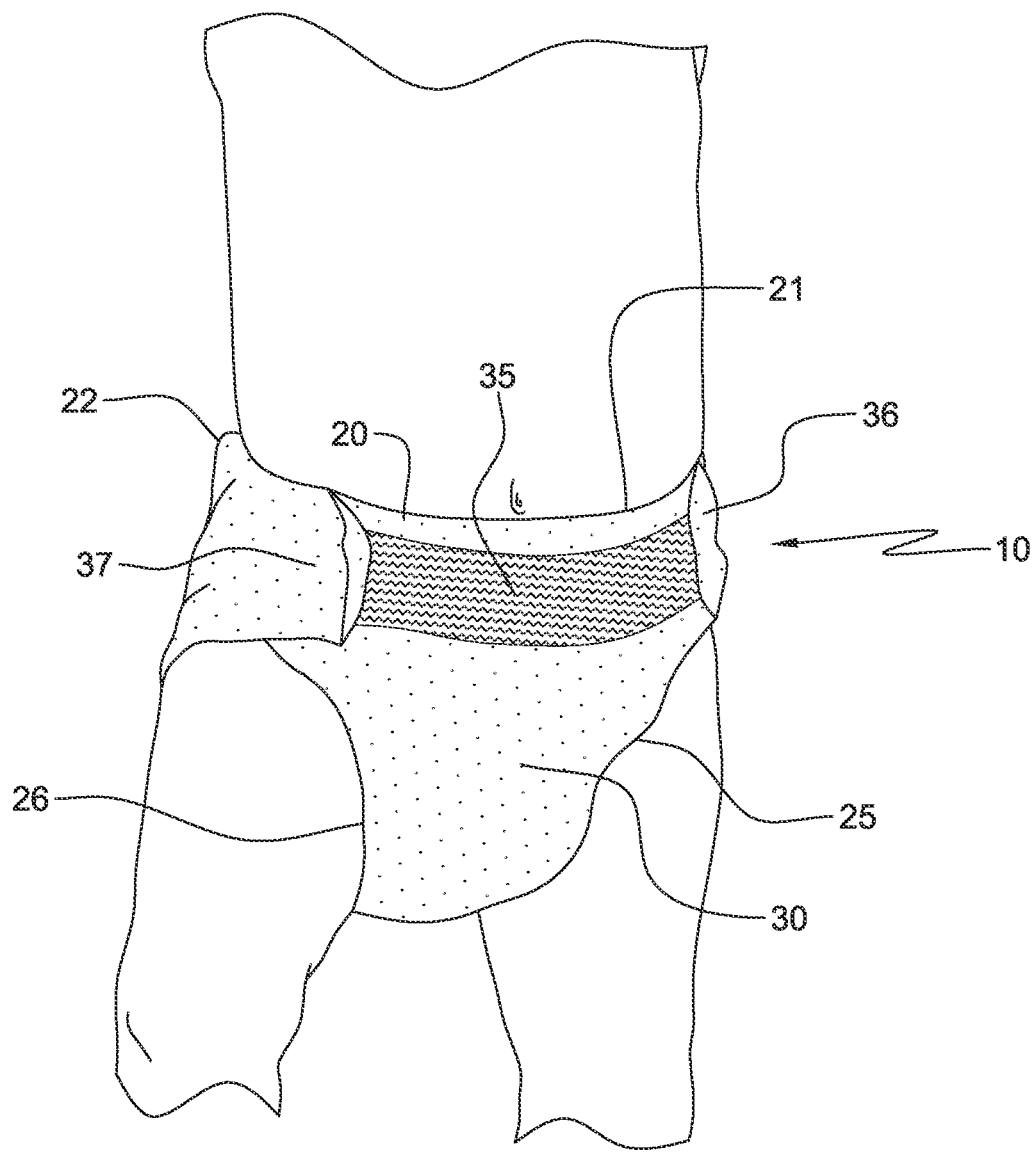
FIG. 8 is a frontal view of the washable diaper of FIG. 1 worn by an infant, in accordance with an aspect of the present invention.
Figure 9:
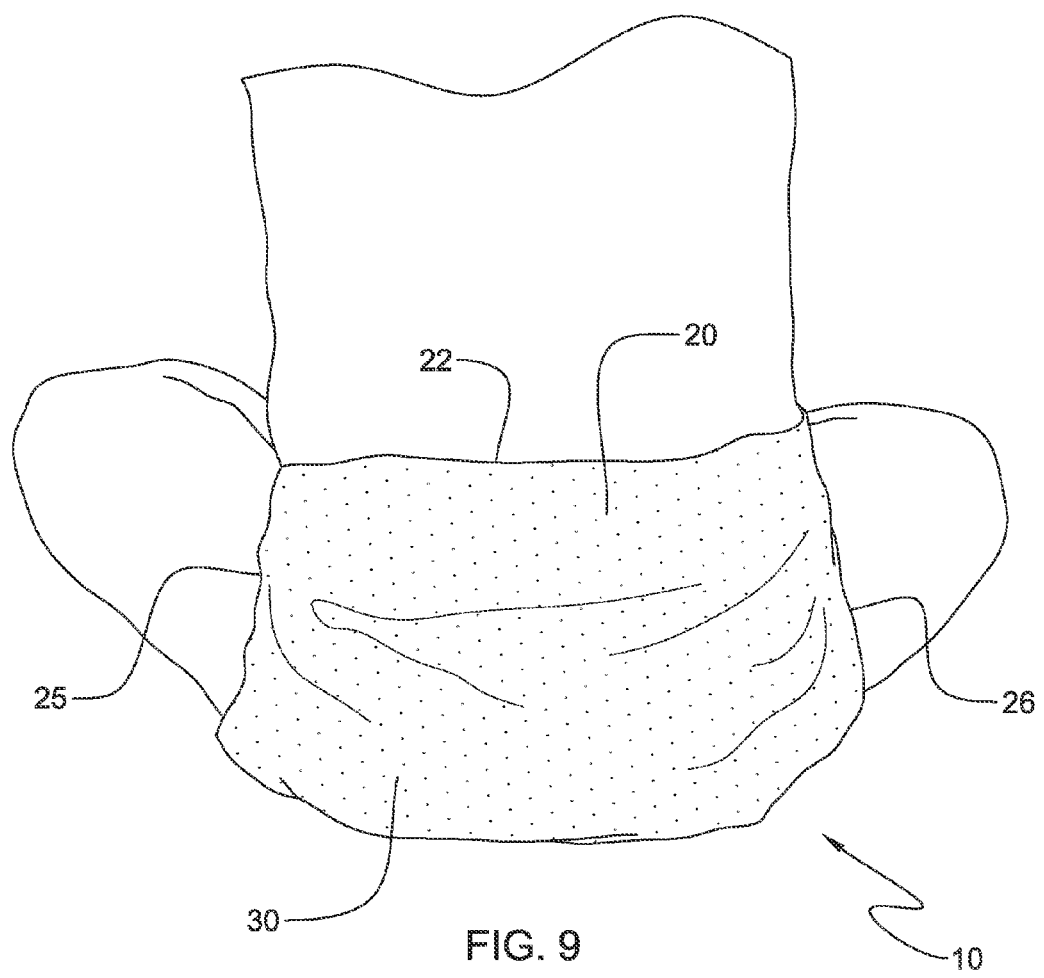
FIG. 9 is a back view of the washable diaper of FIG. 1 worn by an infant, in accordance with an aspect of the present invention.

The fastening mechanisms 33, 34, disposed on extended portions 36, 37 of back end 22 of outer article 20, as depicted in FIGS. 1, 3, 4, 5 and 7, are used to detachably couple to the front of outer article 20, when washable diaper 10 is worn, as shown in FIG. 8. Fastening mechanisms 33, 34 as shown in FIGS. 1, 3, 4, 5 and 7, are hook and loop fasteners, such as the Velcro® brand hook and loop fastener system, but fastening mechanisms 33, 34 may also be one of hook and eye, pin, button, snap button, buckle, or clasp mechanisms.

Figure 2:
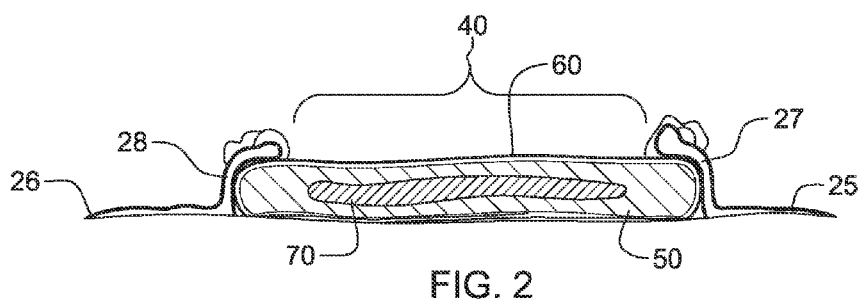
FIG. 2 is an enlarged cross-section view taken along the Line 2-2 of the washable diaper in FIG. 1, in accordance with an aspect of the present invention.

FIG. 2 depicts a cross section of washable diaper 10 of FIG. 1, showing the multiple layers that compose inner liner system 40. Typically, inner liner system 40 is constructed with at least one washable article 50, liner member 60 and at least one absorbent pad 70. Liner member 60 completely surrounds at least one washable article 50. Opposing side barriers 27, 28 further secure inner liner system 40 in outer article 20, so that inner liner system 40 does not shift or move when washable diaper 10 is worn and operate to enhance the containment and absorption of urine and other bodily excrements.

Figure 3:
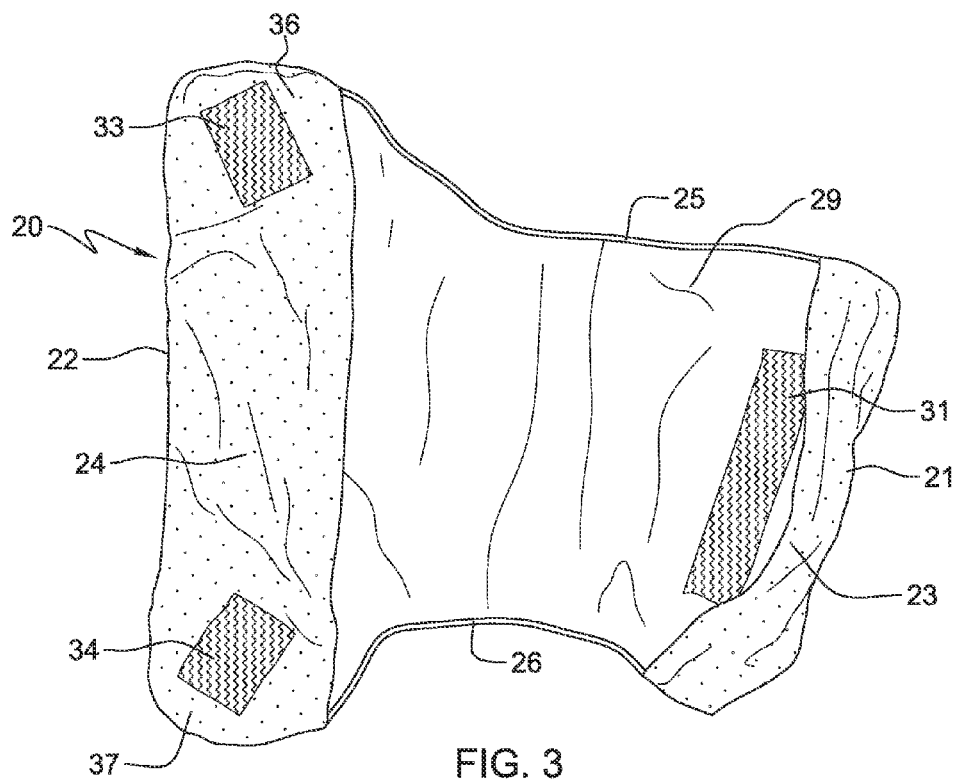
FIG. 3 is a top plan view of another embodiment of the outer article, where the opposing side edges are configured to conform to the body of the wearer of the washable diaper, in accordance with an aspect of the present invention.
Figure 4:
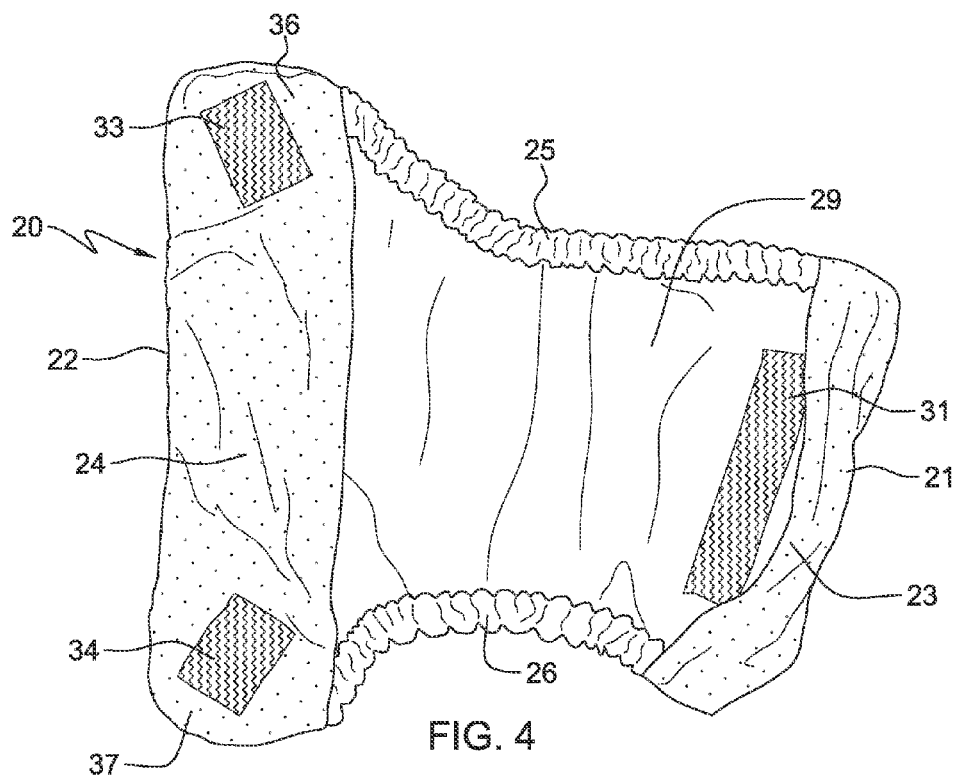
FIG. 4 is a top plan view of another embodiment of the outer article, where the opposing side edges are elasticized to conform to the body of the wearer of the washable diaper, in accordance with an aspect of the present invention.

FIGS. 3 and 4 show additional embodiments of outer article 20 of washable diaper 10. As illustrated in FIGS. 1, 3-5, and 7-9, opposing side edges 25, 26 of outer article 20 are configured to conform to the legs of the wearer of washable diaper 10. Opposing side edges 25, 26 may be elasticized, as shown in FIG. 4, or not, as illustrated in FIG. 3. The contoured configuration of opposing sides 25, 26 of outer article 20 ensures the secure fit of washable diaper 10 and minimizes potential leakage issues. Elasticized opposing side edges 25, 26 as seen in FIG. 4, create a tighter fit on the wearer's legs (see FIG. 8) and provide enhanced protection against leakage.

FIGS. 6A-6C illustrate the method of assembly of liner member 60 and at least one washable article 50. As shown in FIG. 6A, at least one washable article 50 includes opening 53 on first end 51 and opening 54 on second end 52. At least one washable article 50 is usually placed on top of liner member 60 that has first end 61 and second end 62, with three openings 63, 64, 65 on first end 61 and three openings 66, 67, 68 on second end 62. First end 51 of at least one washable article 50 is aligned with first end 61 of liner member 60, and second end 52 of at least one washable article 50 is aligned with second end 62 of liner member 60, so that middle opening 63, 66 of liner member 60 are aligned with openings 53, 54 of at least one washable article 50.

As shown in FIGS. 6B and 6C, the width of liner member 60 is wrapped about at least one washable article 50, so as to wholly surround at least one washable article 50. When liner member 60 is wrapped about at least one washable article 50, openings 64, 65 are aligned with opening 63 on first end of liner member 61 and openings 67, 68 are aligned with opening 66 on second end of liner member 62, as seen in FIG. 6C. Openings 53, 63, 64, 65 are coaxially aligned to represent the composite opening 43 on first end 41 of inner liner system 40 and openings 54, 66, 67, 68 are aligned to represent the composite opening 44 on second end 42 of inner liner system 40.

FIG. 6D depicts an enlarged view of the area identified by the circle noted in FIG. 6C and shows the detailed view of opening 43 on first end 41 of assembled inner liner system 40, that is created by aligning opening 53 on first end 51 of at least one washable article 50 and openings 63, 64, 65 on first end 61 of liner member 60 (shown in FIG. 6C). Composite opening 43 facilitates the ease of detachably coupling inner liner system 40 to outer article 20 using at least one fastening mechanism 31, 32.

FIGS. 8 and 9 show washable diaper 10 being worn by an infant. As seen in FIG. 8, front end 21 of outer article 20 is configured to fit on the front of the infant, with back end 22 of outer article 20 covering the infant's bottom (see FIG. 9).

Fastening mechanism 35 is located on outer surface 30 of front end 21 of outer article 20. Extended portions 36, 37 of back end 22 of outer article 20 are wrapped around the infant to detachably couple to front end 21 of outer article 20. Fastening mechanism 35 as shown in FIG. 8 depicts a strip of one part of the hook and loop fastener. Additionally, fastening mechanism 35 may be made of several latching mechanisms including hook and eye, pin, button, snap button or clasp constructs.

FIGS. 10-12 and 14-19 show another exemplary illustrated embodiment of a washable diaper generally indicated by the reference numeral 110. Exemplary washable diaper 110 is similar to washable diaper 10 described above in connection with FIGS. 1-9, and therefore like reference numerals preceded by the number "1" are used to indicate like elements. The description above with reference to exemplary washable diaper 10 may therefore apply to particular components, systems, features or the like of exemplary washable diaper 110 and is not repeated hereinafter for brevity. Like exemplary illustrated washable diaper 10, exemplary illustrated washable diaper 110 includes an exemplary outer article 120 and an exemplary inner liner system 140.

Figure 10:
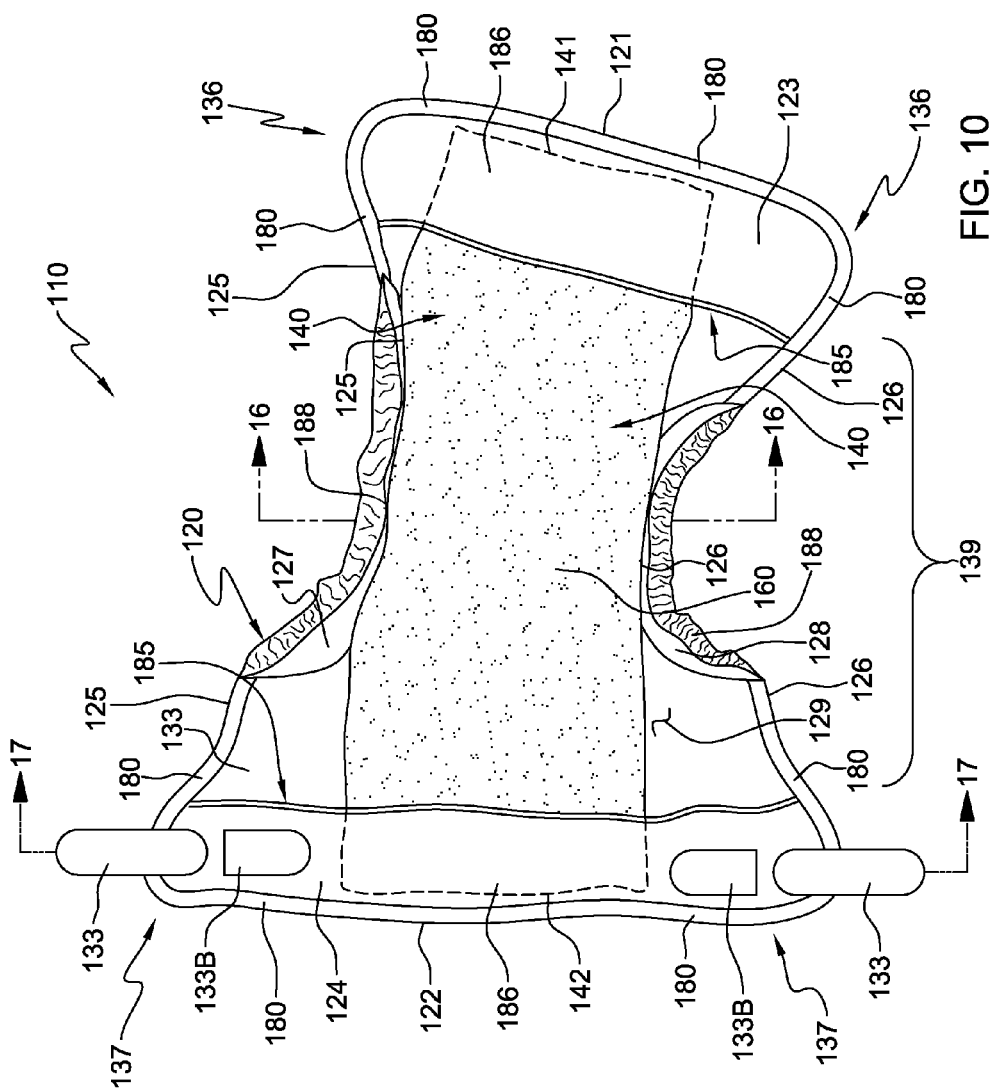
FIG. 10 is a top plan view of another embodiment of a washable diaper, showing an assembled inner liner system detachably coupled to an outer article, in accordance with an aspect of the present invention.

As illustrated in FIG. 10, one exemplary embodiment of washable diaper 110 may be an assembly of an outer article 120 and an inner liner system 140. The inner liner system 140 may be any system or component that is capable of mating with the outer article 120 such that the washable diaper 110 can be worn by a user. As shown best in FIG. 14, the inner liner system 140 may include at least one of an absorbent pad 170, a washable article 150 and a liner member 160. As discussed further below with respect to FIGS. 14-16, in some embodiments the at least one washable article 150 may include an opening 155 in communication with a cavity 154. The opening 155 and cavity 154 may be configured to accept and retain at least one absorbent pad 170 therethrough/therewithin at least when the inner liner system 140 is assembled with the outer article 120 to form the washable diaper 110. As also discussed further below, the at least one washable article 150 may be configured (e.g., the opening 155 and cavity 154 may be configured) such that the at least one absorbent pad 170 is easily removable, such as being consistently removed during a wash cycle of a typical washing machine.

As shown in FIGS. 10-12, 14 and 17, the outer article 120 may include front compartment, flap, pouch or pocket 123 at a front end 121 and a second compartment, flap, pouch or pocket 124 at a second end 122. The first and second compartment 123, 124 may be formed, at least in part, by a first member, component, portion or material 185 and a second member, component, portion or material 186 adjacent or laying over the first member 185. In this way, first and second compartment 123, 124 are formed by the space or area between the first and second member 185, 186. The front and back ends 121, 122, may also include at least one stiffening member or configuration such that the front and back ends 121, 122, and the portions proximate thereto, are relatively stiff as compared to portions without the stiffening members and, thereby, are prevent from folding or otherwise deforming into a "closed" orientation.

Figure 11:
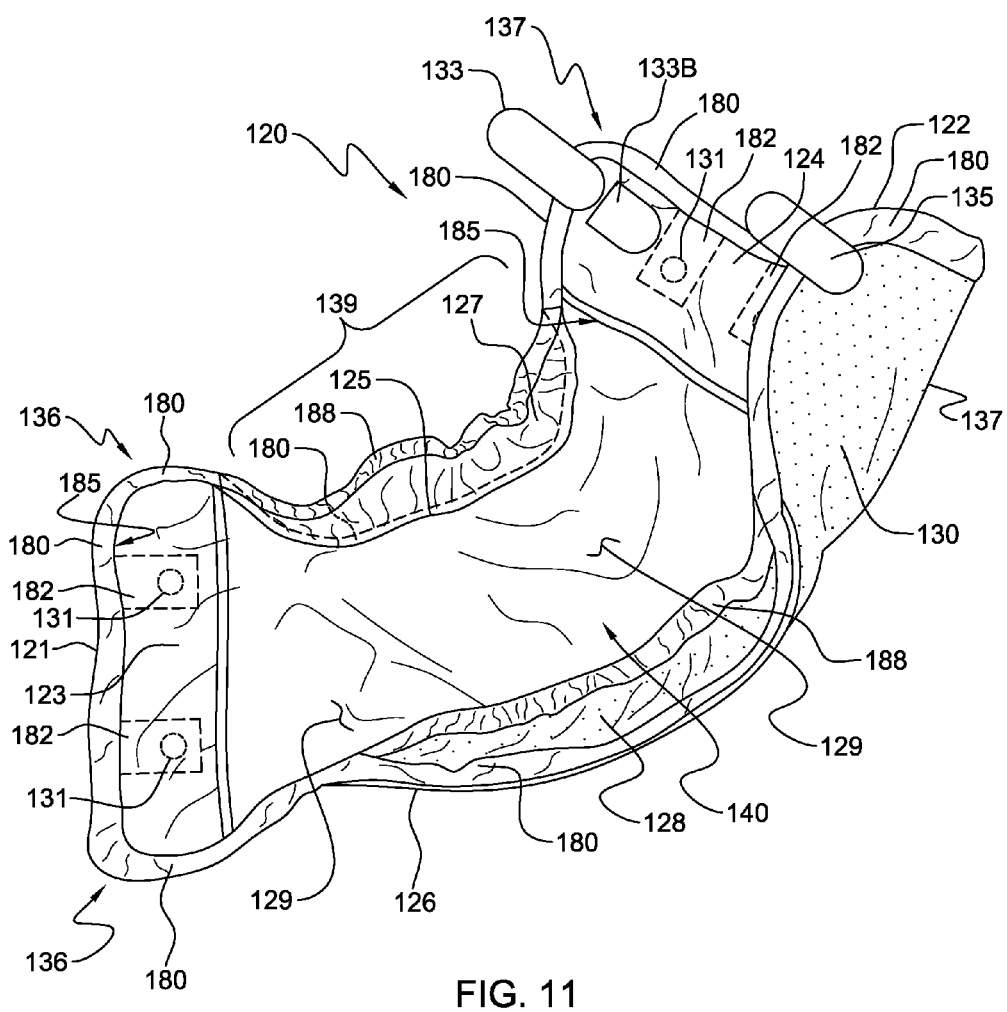
FIG. 11 is a perspective view of the washable diaper of FIG. 10, showing the inner surface of the outer article including the first and back compartments, in accordance with an aspect of the present invention.
Figure 12:
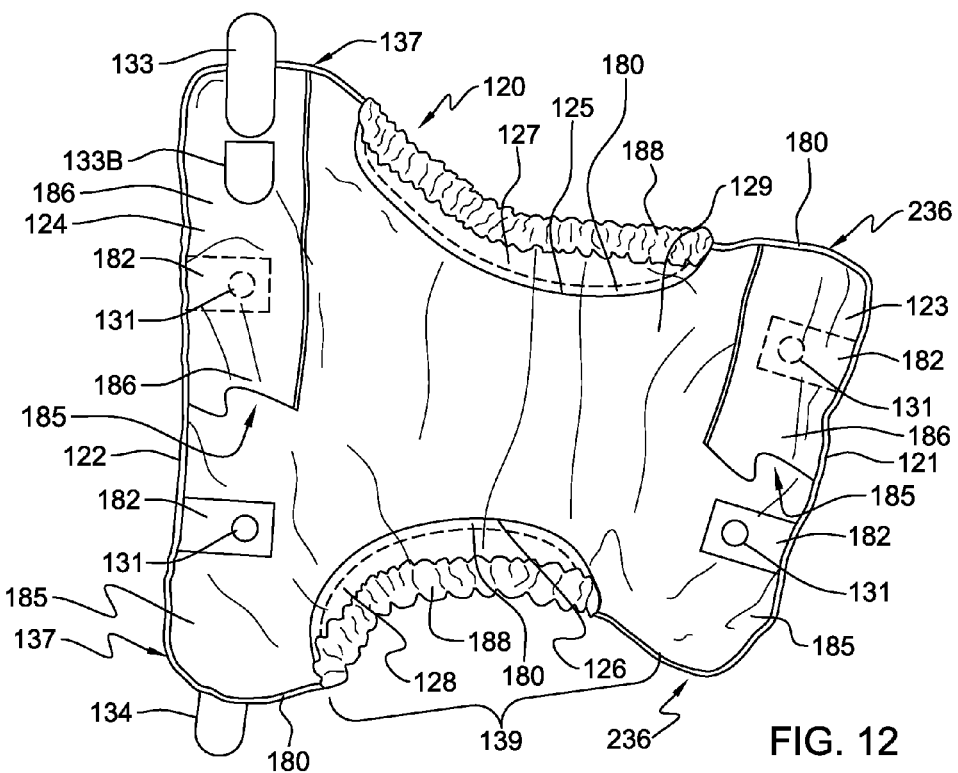
FIG. 12 is a top plan view of the washable diaper of FIG. 10 showing elasticized side barriers and the interior of the outer article, in accordance with an aspect of the present invention.
Figure 14:
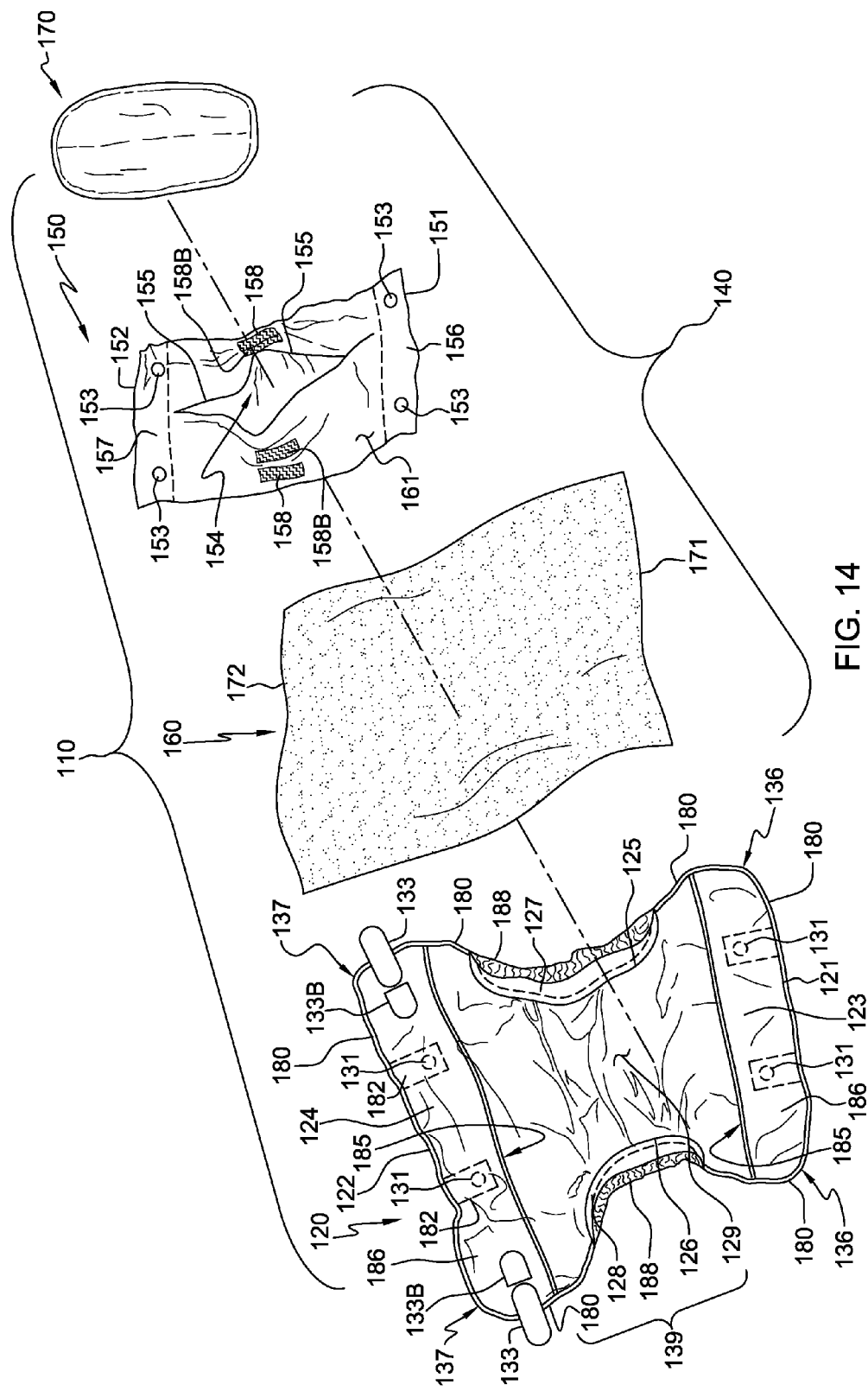
FIG. 14 is an exploded perspective view of the washable diaper of FIG. 10, showing an outer article, a inner liner system that includes at least one flushable liner, at least one washable article, and at least one absorbent pad, in accordance with an aspect of the present invention.

In some embodiments, the first member 185 may be a portion of the inner lining or material that forms the inner surface 129 of the outer article 120, as shown in FIGS. 10-12, 14, 16 and 17. As described above, the inner surface 129 may be substantially liquid impervious. In such an embodiment, the inner surface 129 may span substantially along the entire length of the outer article 120. In contrast, the second member 186 of the first and second compartments 123, 124 may be substantially aligned along the first and second ends 121, 122, respectively, of the inner surface 129 (and therefore the outer article 120 itself), but may only extend partially towards the longitudinal center of the outer article 120. The second portion 186 may therefore be the portion of the inner surface 129 that lies adjacent to the first portion 185. In this way, the first and second compartments 123, 124 may be positioned adjacent the first and second ends 121, 122 of the outer article 120, respectively, and a medial portion 139 of the inner surface 129 of the outer article may be void (or not covered by the second portion 186), as shown in FIGS. 11,12 and 14.

The first and second compartment 123, 124 may be include an opening that faces the medial portion 139 of the outer article 120 (and the inner surface 129), as shown in FIGS. 10-12 and 14. However, besides the opening or passageway facing the medial portion 139 of the outer article 120, the first and second compartment 123, 124 may be operably coupled such that the first and second compartments 123, 124 formed therebetween is substantially "closed". In the exemplary illustrated embodiment, the first and second compartment 123, 124 are "closed" (apart from the medial openings) such that they are substantially liquid impervious.

As shown best in FIGS. 10 and 11, the first and second compartment 123, 124 (e.g., the first and second portions 185, 186) may be "sealed" (except for the medial facing openings), at least in part, by banding 180. As illustrated in FIGS. 10-12 and 16-19 and described further below, banding 180 may be a substantially liquid imperious material, assembly or the like that is applied over a seam, joint, edge or the like. For example, in some embodiments the banding 180 may be substantially liquid impervious fabric material. The banding 180 may be applied such that the banding 180 seals a joint seam, edge or the like, such as a creating a substantially liquid impervious seal. In some embodiments, banding 180 may be applied over a seam, joint, edge or the like by stitching, such as being stitched with substantially non-wicking thread via a needle. In some exemplary embodiments, the non-wicking thread may be a polyester thread and the needle may be a ball needle. In this manner, banding 180 may be applied to seams, edges, joints or the like of the outer article 120, including any such connections between the first and second portions 185, 186 of the first and second compartments 185, 186 to substantially prevent liquid from migrating through the outer article 120 via a seam, joint, edge or the like therein. In other embodiments, seams, edges, joints or the like of the outer article 120 (or any other component) may be "sealed" in another known manner such that they are substantially liquid impervious.

In the illustrated exemplary embodiment best shown in FIGS. 10-12 and 14, the first and second compartment 123, 124 of the outer article 120 extend substantially along the entire width of the outer article 120 and include banding 180 applied to the first and second portions 185, 186 on the opposing side edges 125, 126 of the outer article 120 (and therefore the first and second compartment 123, 124). In some embodiments, the banding 180 itself is substantially liquid impervious, and the banding 180 is applied to the opposing side edges 125, 126 of the first and second portions 185, 186 in a manner that seals the opposing side edges 125, 126 of the first and second portions 185, 186 such that liquid is substantially prevented from migrating therethrough. In this way, the opposing side edges 125, 126 of the first and second compartment 123, 124 may be substantially liquid impervious. For example, the banding 180 may be sewn over the opposing side edges 125, 126 of the first and second portions 185, 186 with non-wicking thread (such as with a ball needle).

As described above, the first and second members 185, 186 of the first and second compartments 123, 124 may be substantially aligned along the first and second ends 121, 122, of the outer article 120. For example, if the first and second members 185,186 are separate and distinct components, they may be substantially aligned along the first and second ends 121, 122, of the outer article 120. In such an embodiment, the first and second ends 121, 122 of the first and second members 185,186 may be coupled to one another, such as sealed to one another. For example, as shown in the illustrated exemplary embodiment of the outer article 120 in FIGS. 10, 11, 14, 16 and 17, the first and second ends 121, 122 of the first and second members 185,186 of the first and second compartment 123, 124 may include banding 180. In some such embodiments, the banding 180 itself is substantially liquid impervious, and the banding 180 is applied to the first and second ends 121, 126 of the first and second portions 185, 186 in a manner that seals the first and second ends 121, 122 of the first and second portions 185, 186 such that liquid is substantially prevented from migrating therethrough. In this way, the first and second ends 121, 122 of the first and second compartment 123, 124 may be substantially liquid impervious. For example, the banding 180 may be sewn over the opposing first and second ends 121, 122 of the first and second portions 185, 186 with non-wicking thread (such as with a ball needle). In some embodiments, the mechanism that couples the banding 180 to the outer article 120 also acts to couple the first and second portions 185, 186 to one another. For example, in embodiments wherein the banding 180 is applies to the first and second ends 121, 122 via thread, the thread may also act to couple the first and second portions 185, 186 to one another (i.e., the thread may stitch the first and second portions 185, 186 at the first and second ends 121, 122.

In some embodiments of the outer article 120, such as the illustrated exemplary embodiment of FIGS. 10-12 and 14, the first and second members 185,186 of the first and second compartment 123, 124 may be integral, monolithic, one-piece or the like. In such an embodiment, the first and second members 185,186 may be substantially liquid impervious (e.g., the inner surface 129 may be substantially liquid impervious) and folded over upon themselves at the first and second ends 121, 122. The "fold line" between the first and second members 185,186 may thereby define, at least in part, the first and second ends 121, 122 of the first and second compartment 123, 124 (and therefore outer article 120 itself). Also, the "fold line" between first and second members 185,186 may define the bottom of the first and second compartment 123, 124 which opposes the openings facing the medial portion 139 of the outer article 120. In this way, the first and second ends 121, 122 may be substantially liquid impervious. However, for aesthetics and/or wear prevention, in the some embodiments the first and second members 185,186 of the first and second compartment 123, 124 may be integral and the "fold line" between first and second members 185,186 may include banding 180, as shown best in FIGS. 10-12 and 14. For example, the entire outline or outer edges of the outer article 120 may include banding 180, such as singled piece or portion of banding sewn over the entire outline or outer edges of the outer article 120.

As shown in FIG. 10, the first end 141 of inner liner system 140 may be aligned with the front end 121 of the washable article 120 and positioned within the front compartment 123. To this end, the front compartment 123 may configured to receive the first end 141 of the inner liner system 140 therein. For example, the second member 186 of the front compartment 123 may extend along the width of the outer article 120 (a direction extending between the opposing side edges 125, 126 of the washable article 120) a sufficient distance such that the width of the inner liner system 140 is substantially the same or smaller. In the exemplary illustrated embodiment best shown in FIG. 10, the width of the second member 186 of the front compartment 123 is about equal to the width of the outer article 120 and the first member 185 and greater than the width of the inner liner system 140, as indicated by the dashed lines representing the outer edges of the inner liner system 140 in the first compartment 123. Similarly, in the illustrated embodiment the second member 186 of the front compartment 123 extends along the length of the outer article 120 (a direction extending between the first and second ends 121, 122 of the washable article 120) a distance such that a relatively substantial portion of the length of the inner liner system 140 can be positioned within the first compartment 123, as indicated by the dashed lines representing the outer edges of the inner liner system 140 in the first compartment 123 in FIG. 10. In this way, the first end 141 of the inner liner system 140 may be positioned substantially within the first compartment 123 such that any liquid flowing through, or forced from, the first end 141 of the inner liner system 140 (or a portion adjacent thereto) becomes trapped or held within the substantially liquid impervious first compartment 123.

The second compartment 186 of the outer article 120 may be configured substantially similar to the first compartment 185 of the outer article 120, such as described above. Specifically, as shown in FIG. 10 the second end 142 of inner liner system 140 may be aligned with the second end 122 of the washable article 120 and positioned within the back compartment 124. To this end, the back compartment 124 may configured to receive the second end 142 of the inner liner system 140 therein. For example, the second member 186 of the back compartment 124 may extend along the width of the outer article 120 (a direction extending between the opposing side edges 125, 126 of the washable article 120) a sufficient distance such that the width of the inner liner system 140 is substantially the same or smaller. In the exemplary illustrated embodiment best shown in FIG. 10, the width of the second member 186 of the back compartment 124 is about equal to the width of the outer article 120 and the first member 185 and greater than the width of the inner liner system 140, as indicated by the dashed lines representing the outer edges of the inner liner system 140 in the second compartment 124. Similarly, in the exemplary illustrated embodiment the second member 186 of the second compartment 124 extends along the length of the outer article 120 (a direction extending between the first and second ends 121, 122 of the washable article 120) a distance such that a relatively substantial portion of the length of the inner liner system 140 can be positioned within the second compartment 124, as indicated by the dashed lines representing the outer edges of the inner liner system 140 in the second compartment 124 in FIG. 10. In this way, the second end 142 of the inner liner system 140 may be positioned substantially within the second compartment 124 such that any liquid flowing through, or forced from, the second end 142 of the inner liner system 140 (or a portion adjacent thereto) becomes trapped or held within the substantially liquid impervious second back compartment 124.

As shown in FIGS. 11, 12 and 14 with the inner liner system 140 not assembled with the outer article 120, the inner surface 129 may be substantially void and the first and second compartments 123, 124 may include at least one fastening mechanism 131 positioned therein. In FIGS. 11, 12 and 14, the at least one fastening mechanism 131 is shown in dashed lines representing its positioning under second member 186. FIG. 12 also shows the second member 186 of the first and second compartments 123, 124 partially cut away to reveal the at least one fastening mechanism 131 beneath. The at least one fastening mechanism 131 may be coupled to the outer article 120 by any means, and may take the form of any known fastening mechanism in the art. As non-limiting example, the at least one fastening mechanism 131 may be at least one half or mate of a hook and loop fastener, such as a Velcro® brand hook and loop fastener system, a hook and eye fastener, pin fastener, button fastener, snap button or clasp mechanisms, or the like. In the illustrated exemplary embodiment, the at least one fastening mechanism 131 is one half or the mate of a press, spring or snap button that faces away from the first portion 185 and toward the second portion 186. Further, the number and positioning of the at least one fastening mechanism 131 may vary. For example, the at least one fastening mechanism 131 may or may not be positioned within the first and second compartments 123, 124. As another example, multiple fastening mechanisms 131 may be provided, such as being provided within the first and second compartments 123, 124. Still further, at least one fastening member 131 may be provided in one of the first and second compartments 123, 124. The at least one fastening mechanism 131 may be configured to detachably couple the inner lining system 140 to the outer article 120. More specifically, the at least one fastening member 131 may be configured to detachably couple the inner liner system 140 to the outer article 120 such that the first end 141 of the inner liner system 140 and an adjacent portion of the inner liner system 140 is positioned and selectively secured within the first or front compartment 123, and such that the second end 142 of the inner liner system 140 and an adjacent portion of the inner liner system 140 is positioned and selectively secured within the second or back compartment 124.

In the illustrated exemplary embodiment, the first or front and second or back compartments 123, 124 include a pair of fastening mechanisms 131 spaced along the width of the compartments 123, 124, as shown in FIGS. 10-12, 14 and 17. As shown best by the cutaway view of FIG. 12, the illustrated exemplary outer article 120 includes a pair of fastening support members 182 coupled to the outer article 120, and each fastening support member 182 includes a fastening mechanism 131 coupled thereto and positioned within the respective first or second compartment 123, 124. In some embodiments, the fastening support members 182 may be flexible, and may extend from the respective first or second ends 121, 122. For example, the fastening support members 182 may include fabric, at least in part, and may be secured to the outer article 120 at the respective first or second ends 121, 122. In some such embodiments, the mechanism that couples the first and second portions 185, 186 to one another also couples the fastening support members 182 to the outer article 120. For example, in the illustrated exemplary embodiment shown best in FIG. 12 the first and second portions 185, 186 of the first and second compartments 123, 124 are coupled to one another (besides being integral) by banding 180 being stitched over the first and second members 185, 186 at the first and second ends 121, 122, respectively, and the fastening support members 182 are positioned between the first and second portions 185, 186 and aligned at the first and second ends 121, 122 such that the stitching also passes through the fastening support members 182. However, in other outer article 120 embodiments the fastening support members 182 may be coupled to the outer article my any known mechanism or method known in the art. Further, the fastening support members 182 may not be provided, or may not be provided in the first and second compartments 123, 124. For example, the fastening mechanism 131 may be provided on the outer article 120 by any other known mechanism or method, such as being coupled to the inner surface 129 of the outer article, such as to the inner surface 129 of the first or second members 185, 186.

Figure 16:
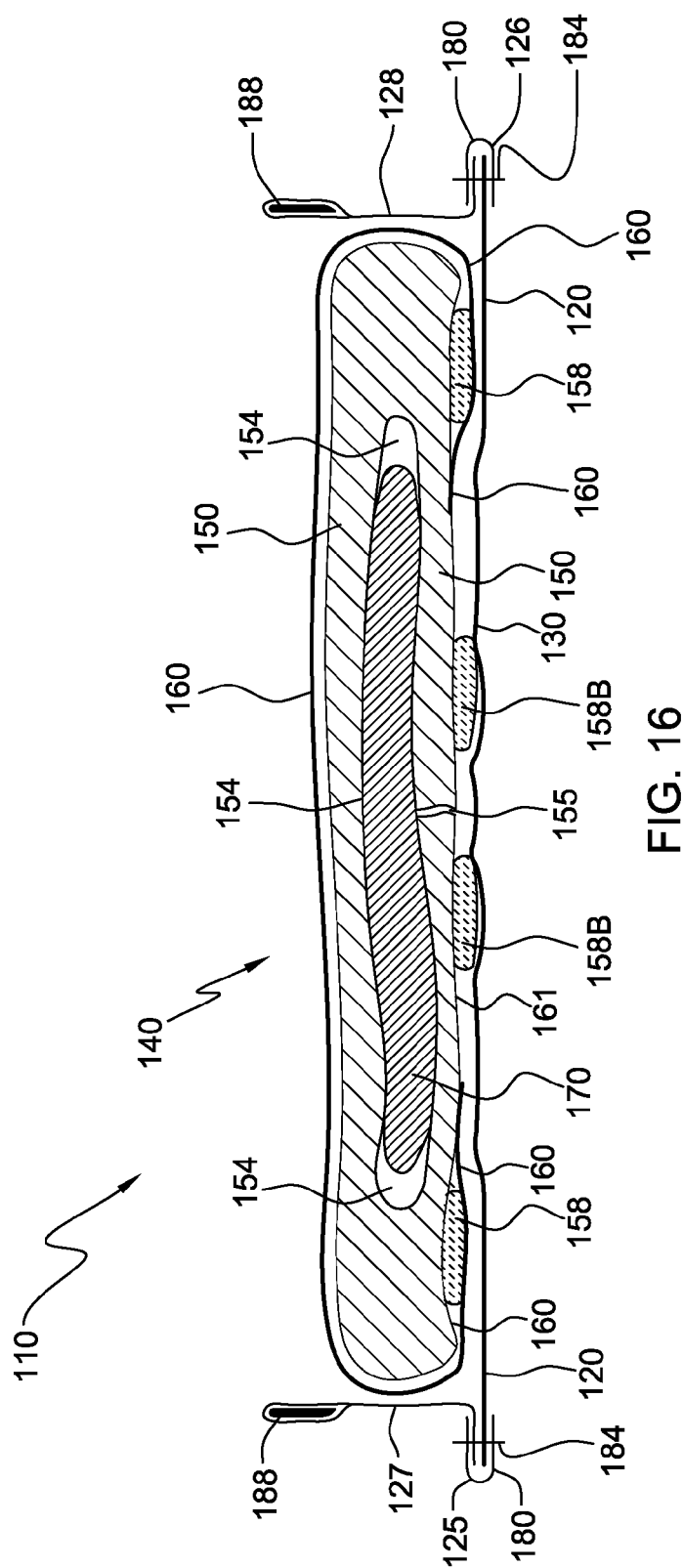
FIG. 16 is an enlarged cross-section view taken along the line 16-16 of the washable diaper of FIG. 10, in accordance with an aspect of the present invention.

As illustrated best in FIGS. 10-12, 14 and 16, the outer article 120 may include first and second opposing side barriers 127, 128 at the medial portion 139 of the outer article 120. The first and second side barriers 127, 128 may extend from the first and second opposing side edges 125, 126 of the outer article 120, respectively, in a direction extending from the outer surface 130 toward the inner surface 139 (i.e., toward the wearer). The opposing side barriers 127, 128 may thereby further secure the inner liner system 140 in the outer article 120 so that inner liner system 140 does not shift or move when washable diaper 110 is worn. The opposing side barriers 127, 128 may thereby also operate to enhance the containment of urine and other bodily excrements in the outer article 120, and consequently operate to enhance the absorption of bodily excrements by the inner liner system 140. In the illustrated exemplary embodiment, the side barriers 127, 128 are distinct or discrete components coupled to the outer article 120. In some such embodiments, the side barriers 127, 128 may be panels tapered at one or both ends with an inner curved surface coupled to the opposing side edges 125, 126 of the inner surface 129, as shown best in FIGS. 11 and 20-22 and described further below. The side barriers 127, 128 may be coupled to the opposing side edges 125, 126 of the outer article 120, respectively, by banding 180. For example, as shown best in the cross-sectional view of the outer article 120 of FIG. 10 in FIG. 16, the curved edge of the side barriers 127, 128 may in abutment with the inner surface 129 of the outer article 120 and banding 180 may be stitched 184 over the outer article 120. More specifically, stitching 184 may pass through an inner portion of the banding 180, the respective side barrier 127, 128, the inner surface 129 and an outer portion of the banding 180 as shown in FIG. 16. If the outer article 120 includes one or more additional layers above the inner layer 129, the stitching 184 may pass through the additional layers as well.

The way in which the side barriers 127, 128 are attached to the outer article 120 may tend to force or encourage the side barriers 127, 128 to extend away from the inner surface 129 toward the body of a wearer, thereby providing a curved shape to the outer article 120 such that the medial portion 139 of the outer article forms a depression or cupped region. For example, the stitching 184 and banding 180 configuration shown in the cross-sectional view of FIG. 16 may act to force the outer edges of the side barriers 127, 128 to extend away from the inner surface 129 to form a "U" shape. By extending away from the inner surface 129 of the outer article, the side barriers 127, 128 may provide a space between the wearer and the inner surface 129 for the inner liner system 140 and the anatomy of the wearer so that the outer edges of the side barriers 127, 128 abut and conform to the wearer and prevent leakage.

The side barriers 127, 128 may include an elasticized member or portion 188 which may additionally contribute to the positioning of the side barriers 127, 128 away from the inner surface 129 of the outer article 120. Further, the elasticized member or portion 188 of the side barriers 127, 128 may tend to cup or bow the outer article 120 in the length direction from the front or first side 121 to the second or back end 122, as shown best in FIG. 11. The cupping or bowing of the outer article 120 in the length direction may enhance the fit and comfort of the washable diaper 110. For example, the elasticized side barriers 27, 28 may be configured to conform to the legs of the wearer and minimize potential leakage out from within the interior of the outer article 120.

In some embodiments, as shown in FIGS. 10-12, 14 and 16 the elasticized member or portion 188 of the side barriers 127, 128 may be the outer edges of the side barriers 127, 128. The elasticized member or portion 188 of the side barriers 127, 128 may take any form such that in a neutral position the elasticized member or portion 188 is capable of being stretched at least lengthwise so the outer article 120 "flattens" out. Stated differently, the elasticized member or portion 188 of the side barriers 127, 128 may take any form such that in a neutral position the side barriers 127, 128 tend to pull or form the outer article into a cupped or bowl shape (see FIG. 11). As shown in FIG. 11, the exemplary elasticized member or portion 188 of the exemplary illustrated side barriers 127, 128 is an elasticized member 188 coupled to the outer edges of the side barriers 127, 128. Further, as shown in FIGS. 10-12 and 14 the exemplary elasticized member or portion 188 of the exemplary illustrated side barriers 127, 128 is coupled to their respective side edge 125, 126 of the inner layer 129 as opposing ends.

Figure 13:
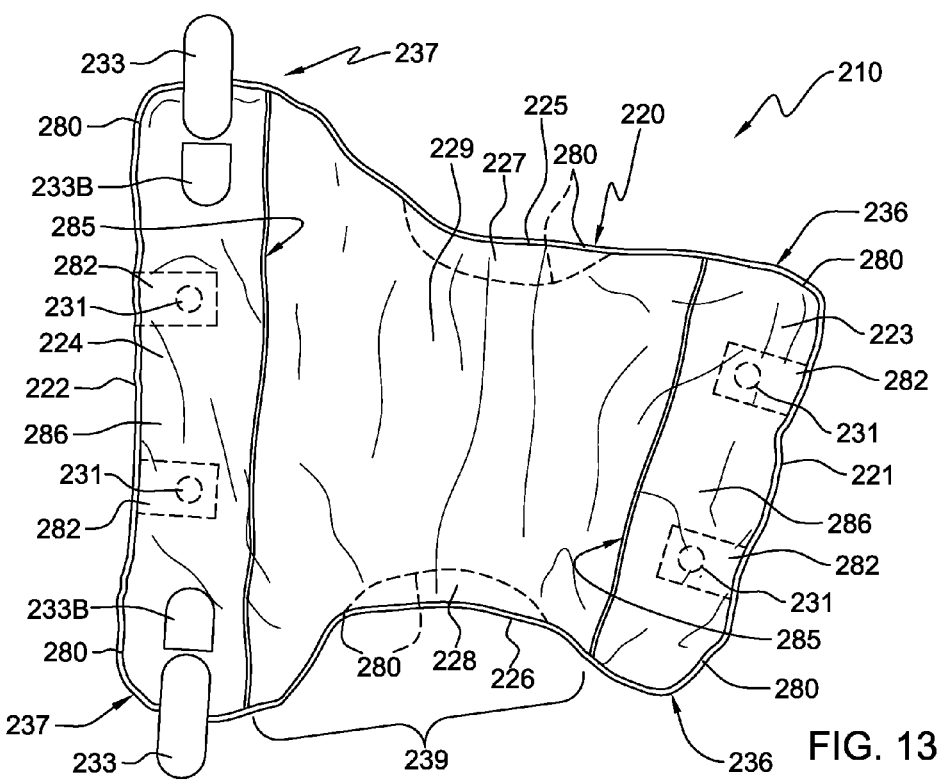
FIG. 13 is a top plan view of another embodiment of an outer article, where the opposing side edges are integral with the outer article and are not elasticized, in accordance with an aspect of the present invention.

In some alternative embodiments, the outer article 120 may not include separate and distinct side barriers 127, 128, such as exemplary outer article 220 illustrated in FIG. 13. In some such embodiments, the inner layer or surface 229 of the outer article 220 may include substantially the same shape and size as compared to an outer article that includes separate and distinct side barriers coupled to opposing sides. In some embodiments however, the outer article 220 may be shaped and sized substantially similar to the outer profile and size of an outer article that includes separate and distinct side barriers coupled to opposing sides. In this way, the side barriers may be in essences integral with the outer article, such as integral with the inner layer or surface 229 and the outer article 220 retains the advantages of the side barriers, as shown in FIG. 13. As also shown in FIG. 13, in some such embodiments the outer article 220 may include banding 280 about its side portions along an internal portion of the outer article in locations where separate and distinct side barriers would be attached to the outer article (such as to the inner surface or portion 229). In this way, the integral side barriers 227, 228 may tend to extend away from the inner layer or surface 229 and toward the user to include the advantageous fit, leakage and aesthetic properties or benefits described above with respect to outer article 120 and side barriers 127, 128.

Figure 18:
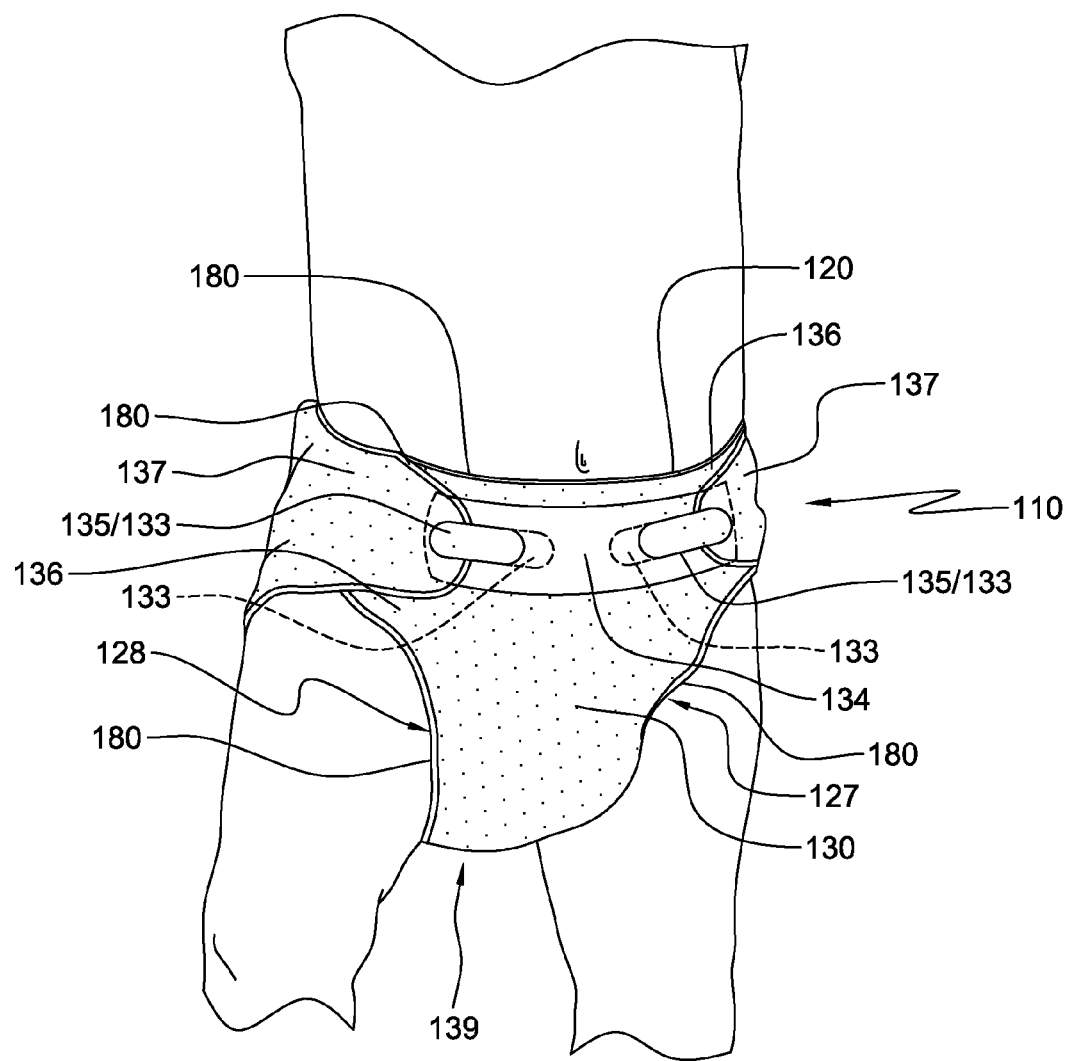
FIG. 18 is a front view of the washable diaper of FIG. 10 worn by an infant, in accordance with an aspect of the present invention.

FIGS. 10-12, 14 and 19 best illustrate the shape of the exemplary outer article 120. The shape and size of the outer article 120, and therefore the washable diaper 110 in general, may be configured such that the washable diaper 110 surrounds or otherwise conforms to the legs and waist of the wearer to maximize fit and minimize potential leakage. For example, the exemplary illustrated outer article 120 is configured with a generally hourglass-like silhouette with the front and back ends 121, 122 including first and second opposing extended portions 136, 137, respectively, being wider than the medial portion 139. In the illustrated exemplary embodiment, the first extended portions 136, 137 at the back end 122 of the outer article 120 are capable of extending or wrapping around the user's body or waist when worn, as shown in FIG. 18. The second extended portions at the second or back end 122 of the outer article 120 may extend further than the first extended portions 136 at the first or front end 121 (i.e., the second extended portions 137 may be wider than the first extended portions 136), as shown best in FIGS. 10-12 and 14. In some such embodiments, when the washable diaper 110 is worn the second extended portions 137 of the back end 122 of the outer article 120 may wrap around the user's waist and over the outer surface of the first extended portions 136 and the portion extending therebetween (at least in part).

In order to removably couple the second extended portions 137 to another portion of the outer article 120, such as when the washable diaper 110 is being worn by a user and thereby couple the washable diaper 110 to the user, the second opposing extended portions 137 may include first fastening mechanisms 133, as shown in FIGS. 10-12, 14 and 17. The first fastening mechanisms 133 of the second extended portions 137 may be any known fastening mechanism capable of removably coupling the second extended portions 137 with another portion of the outer article 120, such as a portion of the outer surface or layer 130. In some embodiments the first fastening mechanisms 133 of the second extended portions 137 may be one part of a multiple-part fastening mechanism, such as one part of a multiple-part fastening mechanism that is configured to mate with another part of the multiple-part fastening mechanism positioned on another portion of the outer article 120. For example, the first fastening mechanisms 133 of the second extended portions 137 may be one part or member of a hook and loop fastener, such as a Velcro® brand hook and loop fastener system, a hook and eye fastener, pin fastener, button fastener, snap button or clasp mechanisms, or the like. In other embodiments, the first fastening mechanisms 133 of the second extended portions 137 may be a single-part fastening mechanism. In the illustrated exemplary embodiment best shown in FIGS. 10-12, 14, 17 and 18, the first fastening mechanisms 133 comprises one part of a hook and loop fastener and extend from the second extended portions 137 out past the side edges 125, 126 of the outer article. As explained further below, the one or more first fastening mechanisms 133 may be configured to removably mate, couple or attach to one or more second fastening mechanism 134 that is provided on another portion of the outer article 120, such as on the outer surface 130 and adjacent the back end 122.

In some alternative embodiments (not shown), the first fastening mechanisms 133 may include multiple fastening mechanisms and an extension member therebetween, at least one of the multiple fastening mechanisms for mating with the one or more second fastening mechanism 134 of the outer article 120. For example, the first fastening mechanisms 133 may include a fastening mechanism provided on the extended portions 137, and an extension member including a fastening mechanism proximate one end of the extension member for removably coupling with the fastening mechanism provided on the extended portions 137 and another fastening mechanism proximate another end of the extension member for removably coupling with a second fastening mechanism 134 provided on the first extended portions 136 or the portions of the outer article 120 thereabout (such as on the outer surface or layer 130 of the first extended portions 136 and/or the portion of the outer surface 130 of the outer article 120 extending between the first extended portions 136 and adjacent the front end 121). In some such embodiments, the fastening mechanism provided on the extended portions 137 of the first fastening mechanisms 133 and the second fastening mechanism 134 may also be configured to removable couple to one another. In such an embodiment, the first fastening mechanisms 133 may allow the outer article 120, and therefore the washable diaper 110, to be worn by both small and large user's because the extension member may or may not be used. Stated differently, in such an embodiment the fastening mechanism provided on the extended portions 137 of the first fastening mechanisms 133 and the second fastening mechanism 134 may be directly removably coupled (without the use of the extension member) to accommodate and removably coupled the washable article 120 (and therefore the washable diaper 110) to a relatively small user, or the extension member may be removably coupled between the fastening mechanism provided on the extended portions 137 of the first fastening mechanisms 133 and the second fastening mechanism 134 to accommodate and removably coupled the washable article 120 (and therefore the washable diaper 110) to a relatively large user.

The second extended portions 137 may also include another fastening mechanism, such as third fastening mechanisms 133B shown in FIGS. 10-12, 14 and 17. The third fastening mechanisms 133B may be any known fastening mechanism. The third fastening mechanism may or may not be deposed or operably attached to the second extended portions 137 of the interior surface 129. The third fastening mechanisms 133B of the second extended portions 137 may be one part of a multiple-part fastening mechanism, such as one part of a multiple-part fastening mechanism that is configured to mate with another part of the multiple-part fastening mechanism. For example, in the illustrated exemplary embodiment the third fastening mechanisms 133B of the second extended portions 137 may be configured to mate with the first fastening mechanisms 133 on the corresponding second extended portions 137. As the first fastening mechanisms 133 of the second extended portions 137 of the exemplary illustrated embodiment are one part of a hook and loop fastener, the third fastening mechanisms 133B may be the other part of the hook and loop fastener such that the first and third fastening mechanisms 133, 133B are capable of removably mating or coupling. In this manner, for example, each second extended portion 137, first fastening mechanism 133 or third fastening mechanism 133B may be deformed such that the first and third fastening mechanisms 133, 133B lie over one another and, thereby, removably couple or attach to one another. As is known in the art, such a configuration may be advantageous if the first fastening mechanisms 133 are configured such that they tend to attach or couple with other portions of the washable diaper 120 or other clothes, fabrics, fastening mechanisms, etc. For example, if the first fastening mechanisms 133 are the hook portion of a hook and loop fastener, the first fastening mechanisms 133 may tend to attach or couple to other portions of the washable diaper 110 or other fabrics when the washable diaper 110 is not worn, such as when the outer article 120 is being washed. In such a configuration, however, the first and third fastening mechanisms 133, 133B may be mated or coupled such that the first fastening mechanisms 133 (or third fastening mechanisms 133B) are blocked-off or otherwise rendered incapable of coupling to other portions of the washable diaper 110 or other fabrics, clothes fastening mechanisms, etc.

In some such embodiments, the outer surface of the first extended portions 136, or portions of the outer article 120 thereabout (such as on the outer surface or layer 130 of the outer article 120 extending between the first extended portions 136 and adjacent the front end 121) may include one or more second fastening mechanism 134, as shown in FIG. 18. The at least one second fastening mechanism 134 may be configured to removably couple with the first fastening mechanisms 133 of the second extended portions 137, such as when the second extended portions 137 are wrapped around a users waist and over the first extended portions 136, as shown in FIG. 18. For example, the at least one second fastening mechanism 134 may be one part of a multiple-part fastening mechanism, such as one part of a multiple-part fastening mechanism that is configured to mate with another part of the multiple-part fastening mechanism. In the illustrated exemplary embodiment the at least one second fastening mechanism 134 is configured to removably mate, couple or otherwise attach to the first fastening mechanisms 133 on the second extended portions 137. As the first fastening mechanisms 133 of the second extended portions 137 of the exemplary illustrated exemplary embodiment of the outer article 120 are one part of a hook and loop fastener, the at least one second fastening mechanism 134 may be the other part of the hook and loop fastener such that the first and second fastening mechanisms 133, 134 are capable of removably mating, attaching or coupling.

The at least one second fastening mechanism 134 may further be configured such that the first fastening mechanisms 133 may couple to the portion of the outer surface or layer 130 adjacent the front end 121 of the outer article 120 in different locations, and thereby accommodate different sized users, fits or tightness/looseness preferences of the washable diaper 110. For example, the at least one second fastening mechanism 134 may include several parts of a multiple-part fastening mechanism that are configured to mate with the first fastening mechanisms 133 positioned in different locations on the outer surface or layer 130 of the outer article 120. As another example, as shown in FIG. 18, the at least one second fastening mechanism 134 may be sized and shaped to expand over a region of the outer surface or layer 130 adjacent the front end 121 of the outer article 120, such as a relatively large portion of one part of a hook and loop fastener (i.e., a relatively large portion of hooks or loops). As the first fastening mechanisms 133 of the second extended portions 137 of the exemplary illustrated exemplary embodiment of the outer article 120 are one part of a hook and loop fastener, the at least one second fastening mechanism 134 may be a relatively large portion of the other part of the hook and loop fastener such that the first fastening mechanisms 133 are capable of removably mating, attaching or coupling to the second fastening mechanism 134 in a variety of location and orientations, as indicated by the dashed outlines of the first fastening mechanisms 133 in FIG. 18. In this way, the second extended portions 137 may be extended over the first second extended portions 136 and the front portion of the outer article 120 to differing extends based on the size or preference of the user.

Figure 17:
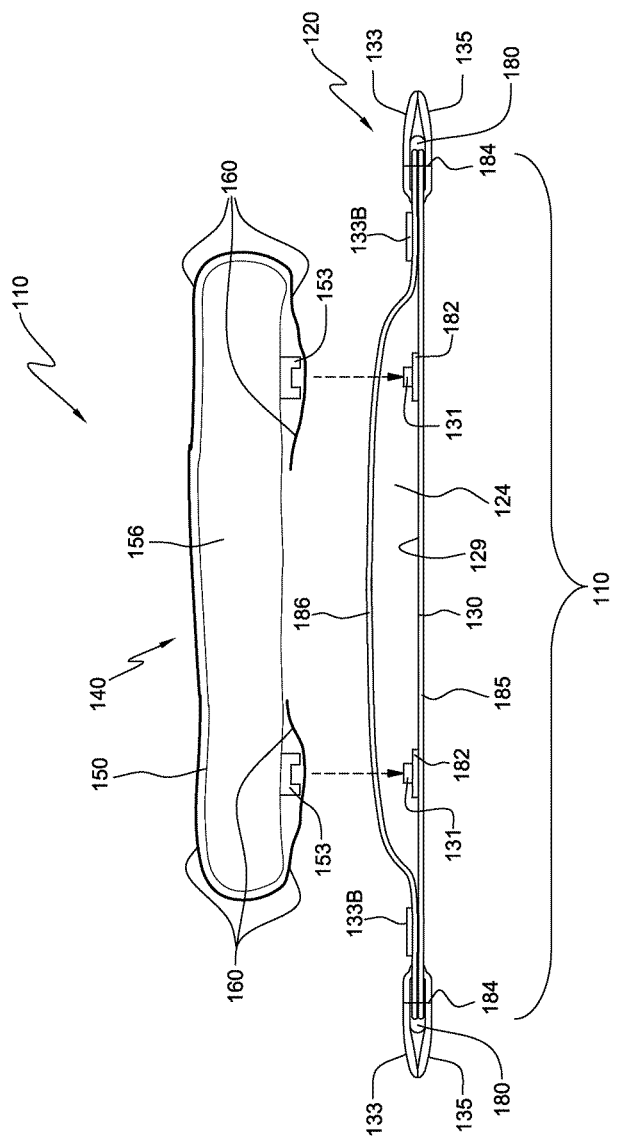
FIG. 17 is an enlarged cross-section view taken along the line 17-17 of the washable diaper of FIG. 10, in accordance with an aspect of the present invention.

As illustrated in FIGS. 11, 17 and 18, the second extended portions 137 may include fourth fastening mechanisms 135 positioned on the outer surface or layer 130 of the outer article 120. For example, the fourth fastening mechanisms 135 may be sized and shaped substantially similar to the first fastening mechanisms and attached directly to the corresponding opposing side of the second extended portions 137 of the outer article 120 (i.e., the outer side 130 as opposed to the inner side 129). The fourth fastening mechanisms 135 may be any known fastening mechanisms. The fourth fastening mechanisms 135 of the second extended portions 137 may be one part of a multiple-part fastening mechanism, such as one part of a multiple-part fastening mechanism that is configured to mate with another part of the multiple-part fastening mechanism. For example, in the illustrated exemplary embodiment the fourth fastening mechanisms 135 of the second extended portions 137 may be configured to mate with the first fastening mechanisms 133. As the first fastening mechanisms 133 of the second extended portions 137 of the exemplary illustrated embodiment are one part of a hook and loop fastener, the fourth fastening mechanisms 135 may be the other part of the hook and loop fastener such that the first and fourth fastening mechanisms 133, 135 are capable of removably mating or coupling.

In this manner, for example, when the washable diaper 100 is worn and the outer article 120 is wrapped around the user's waist and legs, the second extended portions 137 may overlap the first extended portions 136 and the portion of the outer surface 130 extending between the first extended portions 136 such that one first fastening mechanisms 133 completely or fully couples to the at least one second fastening mechanism 134 and the other of the first fastening mechanisms 133 partially or fully overlaps it. Such a configuration may result from a user being relatively small as compared to the size of the washable diaper 110. In such a scenario, the "overlapping" first fastening mechanism 133 may partially removably couple to the at least one second fastening mechanism 134 and partially removably couple to the first fastening mechanism 133 that is completely or fully coupled to the at least one second fastening mechanism 134. In this manner, the fourth fastening mechanisms 135 may provide the outer article 120 with greater flexibility or use with differing sized users.

Turning to the inner liner system 140, as shown in FIGS. 14-17 the inner liner system 140 may include at least one washable article 150, at least one liner member 160 and at least one absorbent pad 170. In some alternative embodiments of the washable diaper 110, however, an absorbent pad 170 may not be provided in the washable article 150. The at least one washable article 150 may include any material capable of absorbing liquid. For example, the at least one washable article 150 in the illustrated embodiment is made from a sewn, liquid absorbent material, such as a hemp, cotton, flannel or a micro fiber fabric. As shown best in FIGS. 14-15C and 16, the at least one washable article 150 may include an opening 155 in communication with a cavity 154. The opening 155 and cavity 154 may be configured to accept and retain at least one absorbent pad 170 therethrough/therewithin at least while the inner liner system 140 is assembled with the outer article 120 to form the washable diaper 110. The exemplary opening 155 and cavity 154 of exemplary illustrated washable article 150 may be formed by the washable article 150 and extend longitudinally from a first end 151 to second end 152 thereof. The opening 155 may be located in various positions, including on the front side, back side, or either lateral sides of at least one washable article 150 and of any size and shape, so long as opening 155 can accommodate the insertion of at least one absorbent pad 170 within the and cavity 154. For example, the longitudinal length of the opening 155 may or may not be longer than the longitudinal length of the at least one absorbent pad 170. To that end, the cavity 154 in communication with the opening 155 may be in any position within the washable article 150 and may be any size and shape, so long at least one absorbent pad 170 can be positioned therewithin via the opening 155. In the illustrated exemplary embodiments of the washable article 150, the longitudinal lengths of the opening 155 and the cavity 154 are at least about 80% the longitudinal length of the least one absorbent pad 170.

In some embodiments of the washable diaper 110 that include at least one absorbent pad 170, the at least one absorbent pad 170 may include at least one axis of substantial symmetry, such as the exemplary illustrated absorbent pad 170 shown best in FIG. 14. In such exemplary embodiments, the use, advantages characteristics or other performance metrics of the at least one absorbent pad 170 may not be affected by the orientation of the at least one absorbent pad 170 along the axis when positioned within the washable article 150. In some embodiments, however, the at least one absorbent pad 170 may be shaped or otherwise configured such that its orientation within the washable article 150 may affect the performance of the at least one absorbent pad 170. In some embodiments, the at least one absorbent pad 170 may be configured specifically for use with either male or female users. For example, the at least one absorbent pad 170 may be shaped differently for use with either male or female users. In other embodiments, the at least one absorbent pad 170 may be the same for both male and female users.

Similarly, in some embodiments the cavity 154 of the washable article 150 and/or the at least one absorbent pad 170 may be configured such that the absorbent pad 170 is positioned within the washable article 150 such that when the inner liner system 140 is coupled to the outer article 120 the absorbent pad 170 is positioned within the medial portion 139 of the outer article 120, such as being positioned within the medial portion 139 of the outer article 120 in specific positions for use with either male or female users.

In some embodiments, the size, shape, orientation and material properties of the at least one absorbent pad 170 and the washable article 150, including the opening 155 and cavity 154 thereof, may be configured such that the at least one absorbent pad 170 tends to easily become disengaged from the cavity 154 through the opening 155 when the inner liner system 140 is not assembled with the outer article 120 or the washable diaper 110 is worn. For example, the at least one absorbent pad 170 and the washable article 150 may be configured such that when the washable article 150 is removed from the outer article 120 and the other components of the inner liner system 140, and washed during a typical wash cycle of a typical washing machine, the at least one absorbent pad 170 becomes dislodged from within the washable article 150. In this way, the at least one absorbent pad 170 may advantageously not need to be handled or otherwise manually removed from the washable article 150, such as when the at least one absorbent pad 170 and washable article 150 are soiled.

The at least one washable article 150 may further comprise at least one liner fastening mechanism 158 disposed on a bottom surface 161 thereof, as shown in FIGS. 14, 15 and 17, for at least partially coupling a liner member 160 thereto. For example, as shown in the exemplary illustrated embodiment a pair of side liner fastening mechanisms 158 may be provided on a bottom surface 161 of the washable article 150. The least one liner fastening mechanism 158 and the opening 154 may be provided on the same side of the washable article 150, such as the bottom side or surface 161. The at least one liner fastening mechanism 158 may be any known fastening mechanism capable of coupling the liner member 160. For example, the at least one liner fastening mechanism 158 may be one part of a multiple-part fastening mechanism that is configured to mate with another part of the multiple-part fastening mechanism. In other embodiments, the at least one liner fastening mechanism 158 may be singular and capable of coupling the washable article 150 to a liner member 160. For example, the at least one liner fastening mechanism 158 may be the hook part of hook and loop fastener, such as the Velcro® brand hook and loop fastener system. In such an embodiment, the liner member 160 may be configured to be coupled to the washable article 150 via the at least one "hook" liner fastening mechanism 158, such as being a fabric or fabric-like material.

The at least one washable article 150 may also include one more additional fastening mechanism in addition to the at least one liner fastening mechanism 158. For example, the at least one washable article 150 may also include at least one opening fastening mechanism 158B adjacent each least one liner fastening mechanism 158 and the opening 155, as shown in FIGS. 15-16. The at least one opening fastening mechanism 158B may be any known fastening mechanism. The at least one opening fastening mechanism 158B may be one part of a multiple-part fastening mechanism, such as one part of a multiple-part fastening mechanism that is configured to mate with another part of the multiple-part fastening mechanism. For example, in the illustrated exemplary embodiment the at least one opening fastening mechanism 158B may be configured to mate with the at least one liner fastening mechanism 158. As the at least one liner fastening mechanism 158 of the exemplary illustrated washable article 150 may be one part of a hook and loop fastener adjacent opposing longitudinal sides of the washable article 150, the at least one opening fastening mechanism 158B may be the other part of the hook and loop fastener such that the adjacent opening fastening mechanisms 158B and liner fastening mechanisms 158 are capable of removably mating or coupling. In this manner, for example, the washable article 150 may be deformed such that adjacent opening fastening mechanisms 158B and liner fastening mechanisms 158 are removably coupled or attached and, thereby, the opening 155 is "pulled" to an "open" position as partially shown in FIG. 14 (as compared to the "closed" state shown in FIG. 16).

As is known in the art, such a configuration may be advantageous if the liner fastening mechanisms 158 are configured such that they tend to attach or couple with other portions of the washable diaper 110 or other clothes, fabrics, fastening mechanisms, etc. For example, if the liner fastening mechanisms 158 are the hook portion of a hook and loop fastener, the liner fastening mechanisms 158 may tend to attach or couple to other portions of the washable diaper 110 or other fabrics when the washable diaper 110 is not worn, such as when the outer article 120 is being washed. In such a configuration, however, the liner and opening fastening mechanisms 158, 158B may be removably mated or coupled such that the liner fastening mechanisms 158 (and opening fastening mechanisms 158B) are blocked-off or otherwise rendered incapable of coupling to other portions of the washable diaper 110 or other fabrics, clothes fastening mechanisms, etc. Further, as explained above when the liner and opening fastening mechanisms 158, 158B are coupled or attached the opening 155 is "opened" to an extent. Such an "open" configuration may be advantageous because it may allow the at least one absorbent pad 170 to become easily disengaged from the cavity 154 through the opening 155 when the inner liner system 140 is not assembled with the outer article 120 or the washable diaper 110 is worn. For example, the "open" configuration of the opening 155 via the liner and opening fastening mechanisms 158, 158B may allow the at least one absorbent pad 170 to be freed from the washable article 150 when the washable article 150 is removed or disengaged from the outer article 120 and the other components of the inner liner system 140 and washed during a typical wash cycle of a typical washing machine. In this way, the at least one absorbent pad 170 may advantageously not need to be handled or otherwise manually removed from the washable article 150, such as when the at least one absorbent pad 170 and washable article 150 are soiled.

As shown in FIGS. 14-15C and 17, the at least one washable article 150 may include at least one first end stiffening member or portion 156 positioned proximate to the first end thereof and/or at least one second end stiffening member 157 being positioned proximate to second end 152 thereof. In some embodiments, the least one first and second end stiffening members 156, 157 may include at least one stiffening member (not shown). The at least one stiffening member may be fabricated from a more rigid material than used for the fabrication of the at least one washable article 150. Exemplary stiffing member materials may include fabric, plastic, metal, polymers, elastomers and the like. In the illustrated exemplary embodiment, the first and second end stiffening members 156, 157 are stiffer portions of the washable article 150 as compared to other portions of the washable article, and are formed by the material of the washable article 150 being stitched and/or folded over upon itself at least once. Although the first and second end stiffening members 156, 157 are illustrated at or near the first and second ends 151, 152, they may alternatively be positioned in any location and orientation and be formed in any manner.

The at least one washable article 150 may also include at least one compartment fastening mechanism 153, as shown in FIGS. 14-15C and 17. The at least one compartment fastening mechanism 153 may be configured to couple at least the at least one washable article 150 to the outer article 120, as described above. The at least one compartment fastening mechanism 153 may be coupled to the washable article 150 by any means, and may take the form of any known fastening mechanism in the art. As a non-limiting example, the at least one compartment fastening mechanism 153 may be at least one half or mate of a hook and loop fastener, such as a Velcro® brand hook and loop fastener system, a hook and eye fastener, pin fastener, button fastener, snap button or clasp mechanisms, or the like. As the at least one fastening mechanism 131 of the exemplary illustrated outer article 120 are one half or mate of a press, spring or snap button, the at least one compartment fastening mechanism 153 may be the other half or mate of the press, spring or snap button such that the at least one fastening mechanism 131 of the outer article 120 and the at least one compartment fastening mechanism 153 are capable of removably mating or coupling. Further, the number and positioning of the at least one compartment fastening mechanism 153 of the washable article 150 may vary. For example, the at least one compartment fastening mechanism 131 may be positioned proximate the side and longitudinal edges of the washable article (e.g., a compartment fastening mechanism 131 proximate each corner of the washable article 150) to substantially align with the fastening mechanisms 131 of the first and second compartments 123, 124 of the outer article 120. In such an arrangement, the compartment fastening mechanisms 153 allow the washable article 150 to be removably coupled to the outer article 120 such that the first and second ends 151, 152 of the washable article 150 are removably coupled and secured within the first and second compartments 123, 124 of the outer article 120, respectively, as shown in FIG. 17. Further, because the at least one absorbent pad 170 may be positioned within the cavity 154 of the washable article 150, the at least one absorbent pad 170 may also be removably coupled to the outer article 120 via the compartment fastening mechanisms 131 and the fastening mechanism 153 of the outer article 120.

As shown in FIGS. 14-17, the at least one liner member 160 may also be configured with the at least one washable article 150 such that the liner member 160 is secured to the outer article 120 via the compartment fastening mechanisms 153 of the washable article 150 and the fastening mechanism 131 of the outer article 120, as well as the at least one liner fastening mechanism 158 of the washable article 150. As shown best in FIGS. 15A-C, the at least one liner member 160 may define a first end 171 and a second end 172 and a longitudinal length therebetween. The longitudinal length of the liner member 160 may be substantially similar to the longitudinal length of the washable article 150 extending between the first and second ends 151, 152 thereof. The width of the liner member 160 may be substantially greater to the width of the washable article 150. In other embodiments however, the length of the liner member 160 may be greater to or less than that of the washable article 150, and/or the width of the liner member 160 may be equal to or less than that of the washable article 150.

Figure 15A:
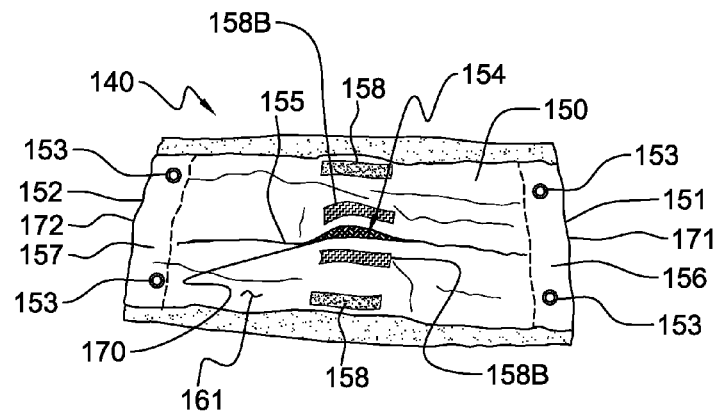
FIG. 15A-C are top plan views of the at least one flushable liner and at least one washable article of the washable diaper of FIG. 10, with the at least one flushable liner being progressively applied to the at least one washable article, in accordance with an aspect of the present invention.
Figure 15B:
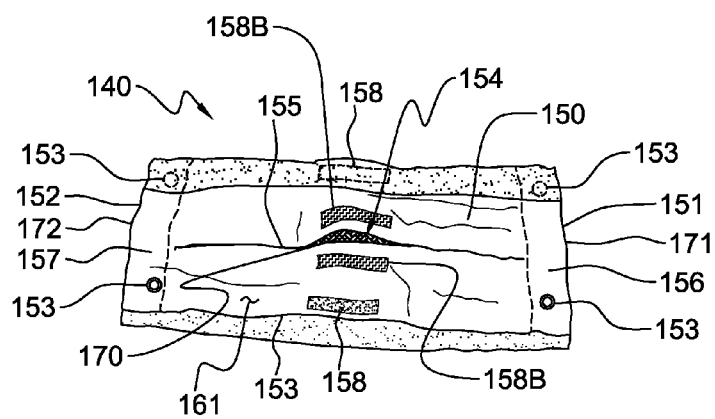
Figure 15C:
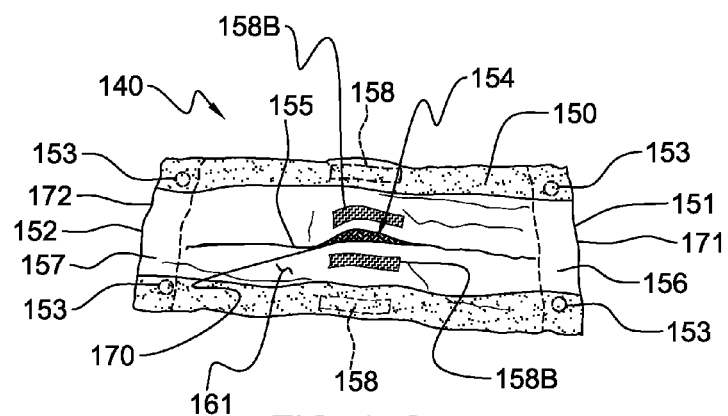

With reference to FIGS. 15A-C, when one embodiment of the washable diaper 110 is assembled, the at least one absorbent pad 170 is inserted through the opening 155 and into the cavity 154 of the washable article 150. As shown in FIG. 15A, once the absorbent pad 170 is positioned within the washable article 150, the top surface (not shown) of the washable article 150 may be positioned on the at least one liner member 160 such that the first and second ends 151, 152 of the washable article 150 substantially align with the first and second ends 171, 172 of the liner member 160 and the washable article 150 is positioned in a medial portion of the width of the liner member 160. Due to the width of the liner member 160 as compared to the width of the washable article 150 and the positioning of the compartment fastening mechanisms 153, the portions of the width of the liner member 160 that expand past the side edges of the washable article 150 may be folded over the washable article 150 such that the liner member 160 at least lies over and substantially covers the compartment fastening mechanisms 153 as shown in FIGS. 15B and 15C. As shown in FIGS. 15B-16, once the liner member 160 is wrapped or folded over the width of the washable article 150, the liner fastening mechanisms 158 of the washable article 150 may engage the liner member 160 at a medial portion of the length of the liner member 160, for example, to at least initially removably secure or attach the liner member 160 to the washable article 150 (and thereby the absorbent pad 170).

Once the liner member 160 is wrapped about the washable article 150 (and therefore the top surface (not shown) of the washable article 150 substantially covers by the liner member 160) and the liner fastening mechanisms 158 of the washable article 150 engage the liner member 120, the inner liner system 140 may be considered formed, constructed or assembled, as shown in FIG. 17. As also shown in FIGS. 10 and 17, the inner liner system 140 may be coupled to the outer article 120 to form the washable diaper 110 when formed, constructed or assembled. As illustrated in FIG. 17, the compartment fastening mechanisms 153 of the washable article 120 and the fastening mechanisms 131 of the outer article 120 may be coupled with the liner member 160 held therebetween. In this manner, the inner liner system 140 can be detachably secured or coupled to the outer article 120 such that the first end 141 of the inner liner system 140 and an adjacent portion thereof is positioned and selectively secured within the first or front compartment 123, and such that the second end 142 of the inner liner system 140 and an adjacent portion thereof is positioned and selectively secured within the second or back compartment 124, as shown in FIG. 10. More specifically and also illustrated in FIG. 10, the inner liner system 140 can be detachable secured or coupled to the outer article 120 such that the first or front ends 151, 171 of the washable article 150 and the liner member 160 and adjacent portions thereof are positioned and selectively secured within the first or front compartment 123, and such that the second ends 152, 172 of the washable article 150 and the liner member 160 and adjacent portions thereof are positioned and selectively secured within the second or back compartment 124. Further, the inner liner system 140 may be held within the medial portion of the width of the outer article 120 by the side barriers 127, 128.

So that the washable article 150 is capable of securing to the outer article 120 via the compartment fastening mechanisms 153 of the washable article 120 and the fastening mechanisms 131 of the outer article 120, in some embodiments the liner member 160 may have a thickness, flexibility and other properties that allows for liner member 160 to be secured between compartment fastening mechanisms 153 and the fastening mechanisms 131 without effectively altering their fastening capabilities. Alternatively, liner member 160 may include apertures (not shown) aligned with the compartment fastening mechanisms 153 and the fastening mechanisms 131 so that they can be coupled together through the liner member 160.

In the illustrated exemplary embodiment, the liner member 160 is generally compliant, soft feeling, and non-irritant to the wearer's skin. In some embodiments, the liner member 160 may be fabricated from a liquid pervious material, including but not limited to, rice paper, cellulose fibers, blend of rayon and cellulose fibers and any other natural or synthetic liquid permeable hydrophobic fibrous materials that will allow liquid to readily penetrate through its thickness. The liner member 160 may also be fabricated from a material that will wick moisture away from the wearer's skin. The liner member 160 may further be fabricated from any material that is biodegradable and flushable through a regular toilet system. When the liner member 160 is fabricated from a liquid pervious, flushable material, it may function to contain non-liquid bodily excrements and allow for easy disposal via a regular septic/sewer system, as well as allow liquid excrement to pass through the liner member 160 and into the washable article 150 and absorbent pad 170.

Figure 19:
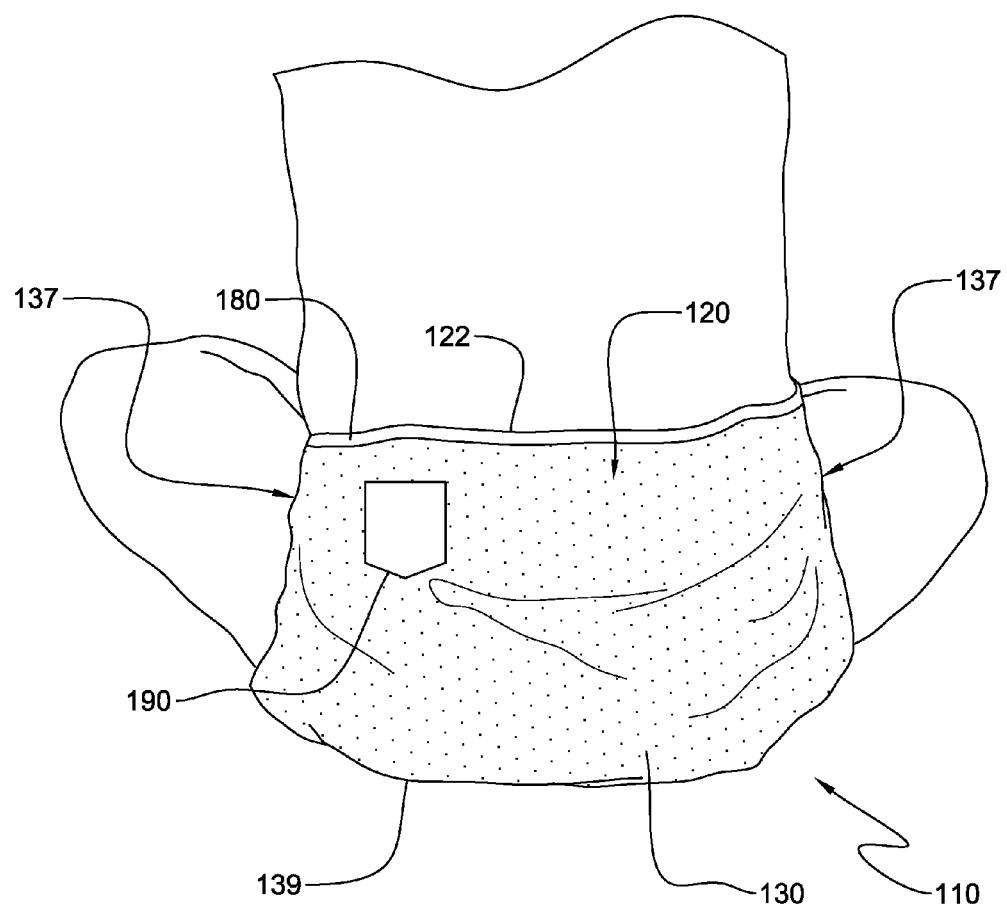
FIG. 19 is a back view of the washable diaper of FIG. 10 worn by an infant, in accordance with an aspect of the present invention.

As shown in FIG. 19, the outer article 120 may include any design or aesthetic pleasing ornamentation on the outer surface or layer 130. For example, the outer surface or layer 130 may include a design, such as a pattern or depiction that an adult or child would find aesthetically pleasing. As another example, as shown in FIG. 19 the outer surface or layer 130 may include ornamentation 190 detachably or permanently coupled thereto that resembles a pocket or other typical "adult" clothing characteristics, such as one or more pocket positioned on the outer surface or layer 130 of the outer article. In some embodiments, the pocket ornamentation 190 may be detachable, and only one pocket ornamentation 190 may be provided on the back side of the outer surface or layer 130 of the outer article 120. Further, in some embodiments the ornamentation 190 on the outer surface or layer 130 of the outer article 120 may serve a utilitarian purpose, such as for storage, identification, style or the like.

Figure 20:
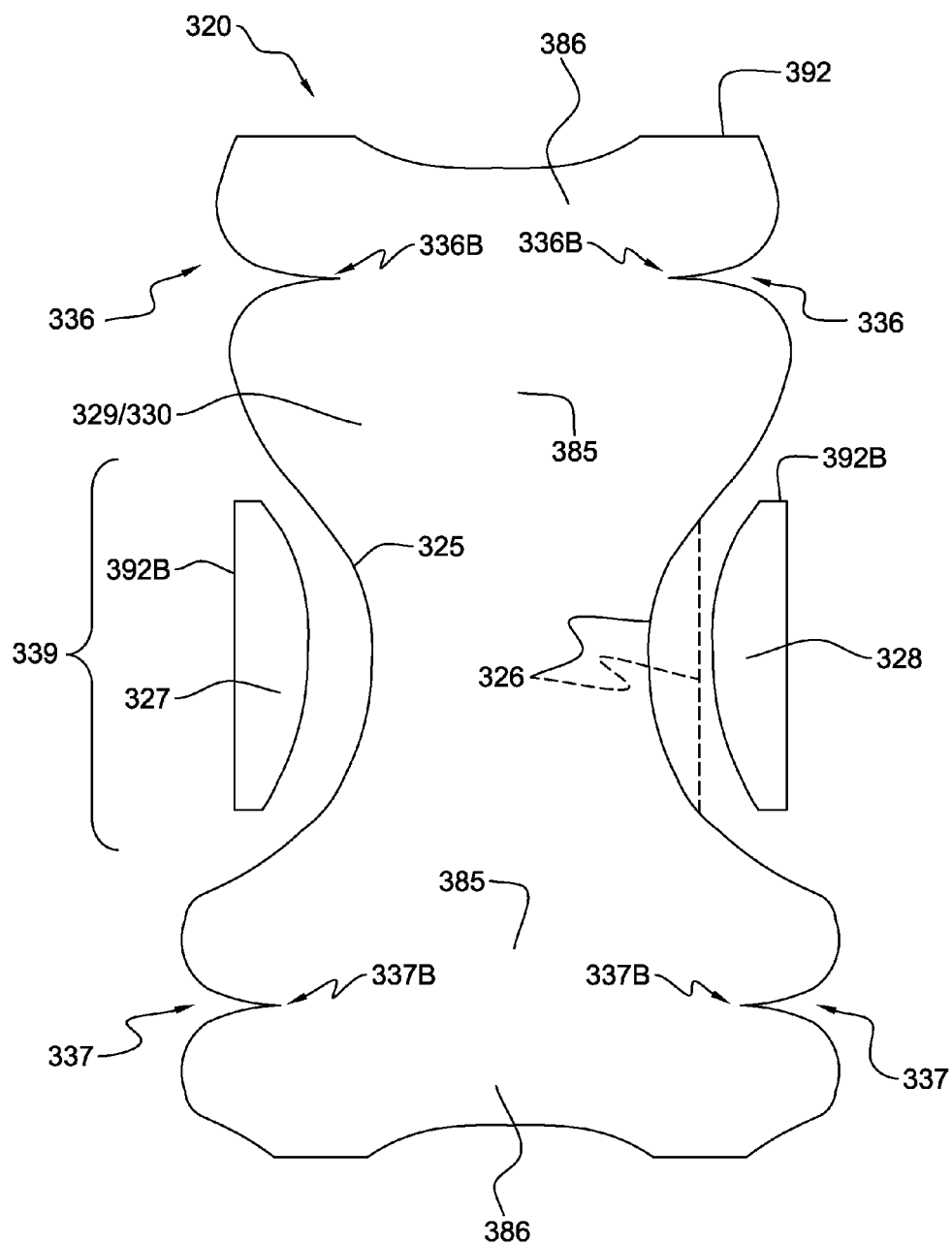
FIG. 20 is a top plan view of another embodiment of an outer article showing a layer of the outer article being initially formed, in accordance with an aspect of the present invention.
Figure 21:
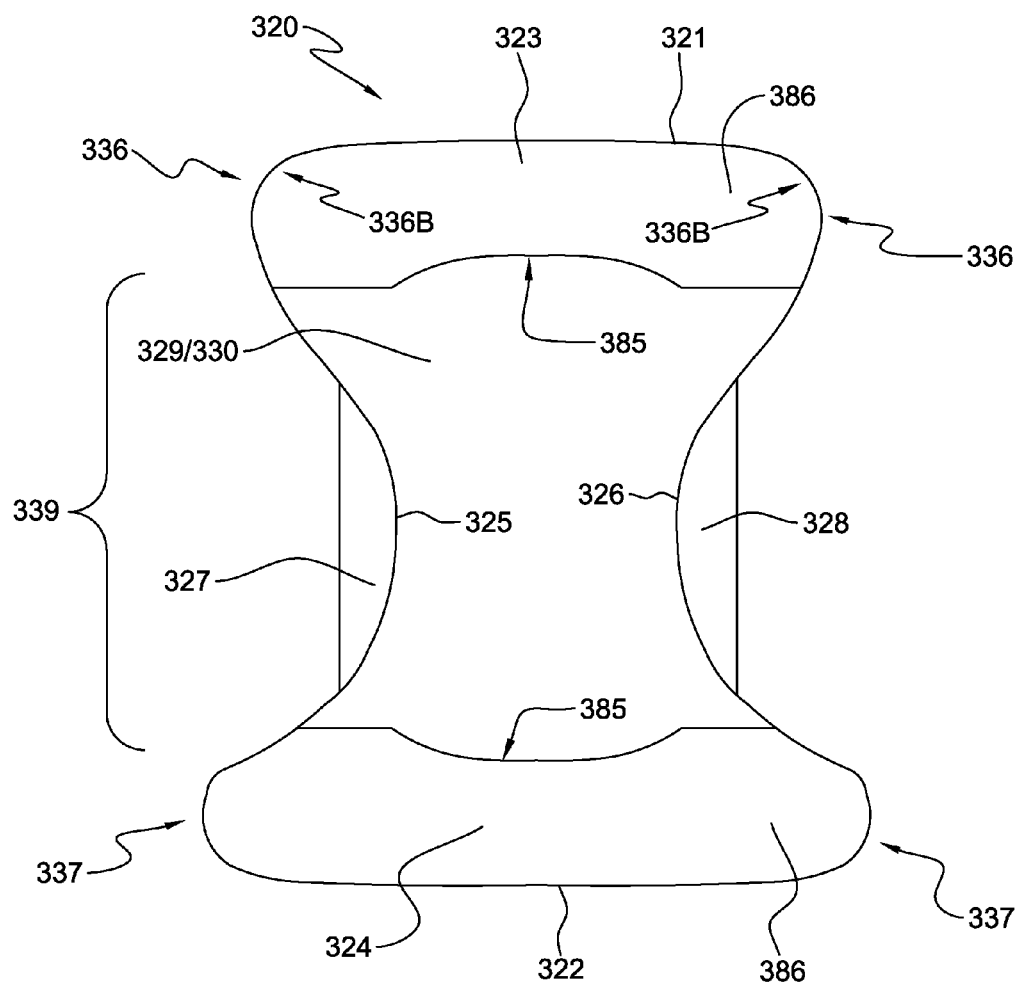
FIG. 21 is a top plan view of the washable diaper of FIG. 20 showing the outer article being further processed, in accordance with an aspect of the present invention.
Figure 22:
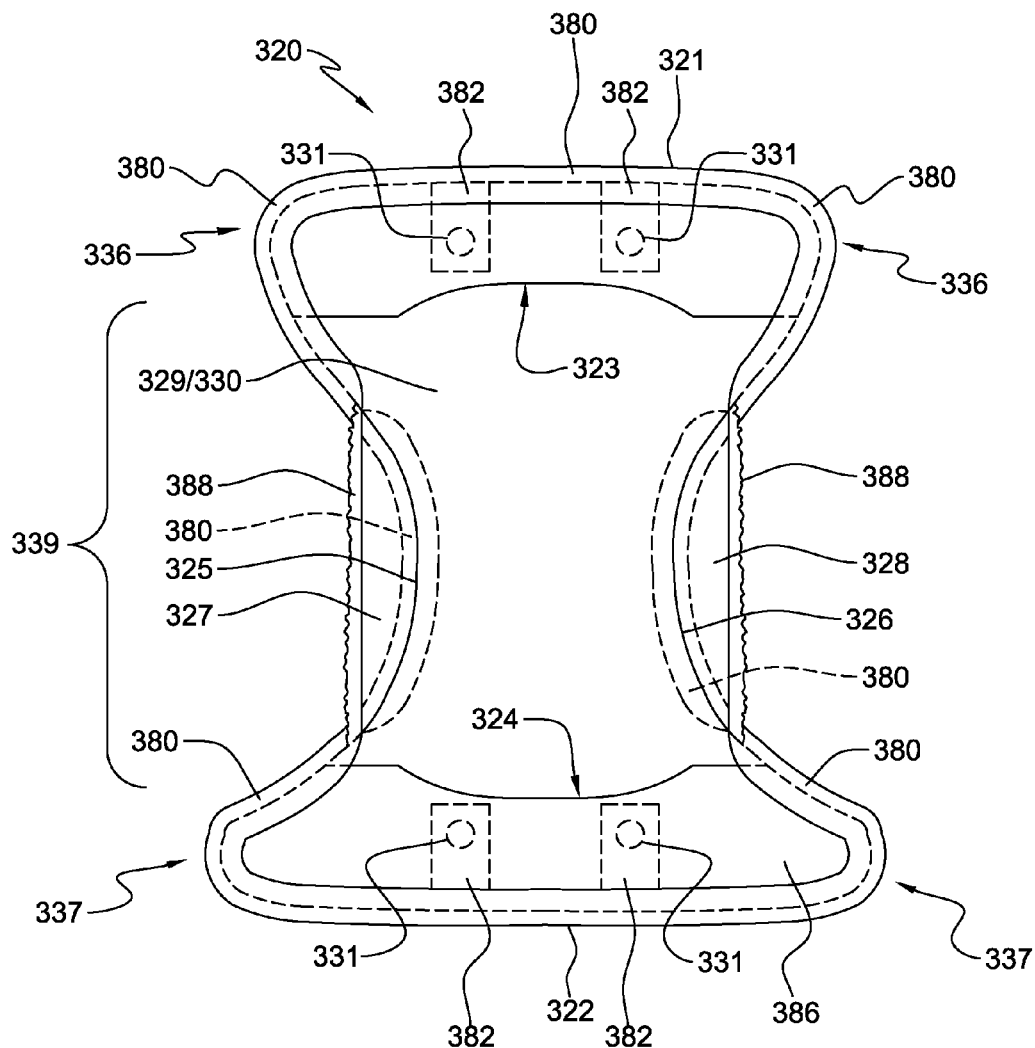
FIG. 22 is a top plan view of the washable diaper of FIG. 20 showing the outer article being still further processed.

Turning to FIGS. 20-22, an exemplary partial method of manufacturing an outer article is shown, and the outer article is generally indicated by the reference numeral 320. Exemplary outer article 320 is similar to the embodiments of exemplary outer articles 20, 120 and 220 described above in connection with FIGS. 1-19, and therefore like reference numerals preceded by the number "3", as opposed to the number "1" or "2", are used to indicate like elements. Like exemplary illustrated outer articles 20, 120 and 220, exemplary illustrated outer article 320 may be assembled with an inner liner system (no shown) to form a washable diaper (not shown). The description above with reference to exemplary outer articles 20, 120 and 220 may therefore apply to particular components, systems, features or the like of exemplary outer article 320 and is not repeated hereinafter for brevity.

As shown in FIG. 20, a method of manufacturing an outer article 320 may comprise the step of removing, forming or otherwise manufacturing a generally hourglass-shaped stock 392 of liquid pervious material or materials. When formed of liquid impervious material, the generally hourglass-shaped stock 392 may be the inner layer 329 of the outer article 320. In some other embodiments, the generally hourglass-shaped stock 392 may be the outer layer 330 of the outer article 320. For example, if the generally hourglass-shaped stock 392 is not formed from liquid impervious material, the generally hourglass-shaped stock 392 may be an outer layer 330. The generally hourglass-shaped stock 392 may be directly removed from a single piece of liquid pervious material, or may be removed in stages or steps. Further, in some embodiments multiple hourglass-shaped stocks 392 are removed from liquid pervious material at the same time, such as stamping a stack of liquid pervious material with a cutter that is shaped substantially similar to the hourglass-shaped stock 392. In some embodiments a template shaped substantially similar to the hourglass-shaped stock 392 may be used to obtain, produce or otherwise manufacture the hourglass shaped stock 392 of liquid pervious material or materials.

The hourglass-shaped stock 392 may include the first and second portions 385, 386 of the first and second compartments 323, 324 as adjacent integral components. In the illustrated exemplary embodiment of the hourglass-shaped stock 392 the first and second opposing extended portions 336, 337 of the first and second portions 385, 386 may include first and second interior extending portions 336B, 337B, respectively, to delineate the first and second portions 385, 386, as best shown in FIG. 20. As explained further below, the first and second interior extending portions 336B, 337B may facilitate the forming or manufacture of the first and second liquid pervious compartments 332, 334. In alternative embodiments, the first and second portions 385, 386 of the first and second compartments 323, 324 may be formed separately, such as forming the hourglass-shaped stock 392 with the first portions 385 and forming the second portions 386 separately (i.e., the second portions 386 may be discrete). Similarly, as shown in FIG. 20 the opposing side barriers 327, 328 may be formed separately from the hourglass-shaped stock 392 as side barriers stock 392B. However, in alternative embodiments the hourglass-shaped stock 392 may include the opposing side barriers 327, 328 integral therewith, as indicated by the dashed line 326 as compared to if the opposing side barriers 327, 328 are formed from separate and distinct side barrier stock 392B, as shown in FIG. 20.

Once an hourglass-shaped stock 392 of liquid impervious material is formed, the hourglass-shaped stock 392 can be further formed into an outer article 320 through additional processing steps. For example, as shown in FIG. 21 the opposing side barriers 327, 328 may be coupled to the opposing sides 325, 326 of the hourglass-shaped stock 392. In some embodiments, the opposing sides 325, 326 of the hourglass-shaped stock 392 may be coupled to the opposing sides 325, 326 of the hourglass-shaped stock 392 by stitching (i.e., sewn thereto). As also shown in FIG. 21, the second portions 386 may be folded over the first portions 385 toward the medial portion 339 of the hourglass-shaped stock 392 at the first and second interior extending portions 336B, 337B. As such, the first and second interior extending portions 336B, 337B may be used as a guide as to where the second portions 386 should be folded over the first portions 385. Thereby, the "fold-line" formed by placing the first and second portions 385, 386 in aligned abutment forms the first and second ends 321, 322 of the outer article 320 and a liquid impervious bottom edge to the first and second compartments 323, 324, respectively.

With the first and second portions 385, 386 in aligned abutment with the second portion 386 overlying the first portion 385, the side edges of the first and second compartments 323, 324 may be sealed such that they are liquid impervious. For example, as shown in FIG. 22, liquid impervious material or portions 380 may be affixed over the side edges of the first and second compartments 323, 324 such that the side edges are substantially liquid impervious. In this way, the side edges and first and second ends 321, 322 of the first and second compartments 323, 324, respectively, are liquid impervious and the portion facing the medial portion 339 of the outer article is "open". In such an embodiment, fastening support members 382 with liner system fastening members 331 may be coupled within the first and second compartments 323, 324. For example, liquid impervious material or portions 380 may be affixed over the front and back sides 321, 322 such that the front and back sides 321, 322 are liquid impervious, and the fastener support members 382 may be coupled to the outer article 320 via the affixing of the material or portions 380. In some embodiments, the liquid impervious material or portions 380 may be banding stitched over the front and back sides 321, 322 with non-wicking thread, and the fastening support members 382 may be positioned adjacent the front and back sides 321, 322 between the first and second portions 385, 386 such that the thread affixes the banding, first and second portions 385, 386 and fastening support members 382 together. In some embodiments, the thread is polyester thread sewn via a ball needle.

As also shown in FIG. 22, the liquid impervious material or portion 380 may be applied over the edges and substantially about the perimeter of the outer article 320, including the side edges 325, 326 where the opposing side barrier 327, 328 are coupled to the outer article 320. In contrast, however, the outer edges of the opposing side barrier 327, 328 may not include the liquid impervious material or portion 380. Instead, the outer edges of the opposing side barrier 327, 328 may include an elastic member 388 coupled thereto. For example, the elastic member 388 may be couple to the outer edges of the opposing side barrier 327, 328 in an elongated or stretched orientation or state, such that in a neutral position the elastic member 388 may act to shorten the longitudinal length of the opposing side barrier 327, 328.

In this way, the opposing side barrier 327, 328 may act to cup or bowl the outer article 320 into a shape that is conducive to being worn as a washable diaper 310. Further, the manner which the opposing side barrier 327, 328 are attached to the side edges 325, 326 of the washable article 320, such as by banding being sewn over the edges thereof, may tend to encourage or promote the opposing side barrier 327, 328 from extending away from the inner surface or layer 339. In such a configuration, the opposing side barrier 327, 328 may be effective in preventing leakage from the interior of the washable article 320 and enhance the comfort and fit of the washable article 320 to a user.

The outer article 320 may include further processing, such the application of fastening mechanism configured to allow the outer article 320 to be wrapped around a users waist and legs and removable coupled thereto. Further, covers or shields for the fastening mechanisms may also be provided to prevent the fastening mechanism from inadvertently "coupling", such as when the outer article 320 is washed. Still further, the washable article may include several layers, and such layers may be coupled together via one or more independent step, or during one of the previously discussed steps. For example, the application of the liquid impervious members or portions 380 may be effective in coupling several layers of the outer article 320 to one another.

As may be recognized by those of ordinary skill in the pertinent art based on the teachings herein, numerous changes and modifications may be made to the above-described and other embodiments of the present invention without departing from the spirit of the invention as defined in the claims. For example, the components of the washable diaper may be made of any of numerous different materials that are currently or later become known for performing the functions of such components. In addition, not all elements or all features disclosed herein are necessary, and if desired, additional elements or features may be added. Further, components, aspects or combinations thereof described with a particular embodiment may be incorporated in another described embodiment to achieve the same or similar function as it achieved in the particular embodiment. Similarly, the components of the washable diaper may take any of numerous different shapes and/or configurations.

Accordingly, this detailed description of the illustrated and exemplary embodiments of the present invention is to be taken in an illustrative, as opposed to a limiting sense.

What is claimed is:

1. A washable diaper comprising:
   an outer article configured with a first end, a second end, and a medial portion with a first concave side edge extending between a first side of the first and second ends and a second concave side edge opposing the first concave side edge extending between a second side of the first and second ends, and further comprising an inner surface and an outer surface;
   a first substantially liquid impervious barrier panel including a first convex side edge and a first linear side edge, wherein a first portion of the first substantially liquid impervious barrier panel proximate to the first convex side edge overlaps the inner surface of the outer article such that the first convex side edge is substantially aligned with the first concave side edge of the outer article, and a second portion of the first substantially liquid impervious barrier panel extends away from the inner surface of the outer article in a direction extending from the outer surface toward the inner surface such that the second portion does not overlap the outer article;

a second substantially liquid impervious barrier panel opposing the first substantially liquid impervious barrier panel including a second convex side edge and a second linear side edge, wherein a first portion of the second substantially liquid impervious barrier panel proximate to the second convex side edge overlaps the inner surface of the outer article such that the second convex side edge is substantially aligned with the second concave side edge of the outer article, and a second portion of the second substantially liquid impervious barrier panel extends away from the inner surface of the outer article in a direction extending from the outer surface toward the inner surface such that the second portion does not overlap the outer article; and at least one member secured over a junction of the first convex side edge of the first substantially liquid impervious barrier panel and the first concave side edge of the medial portion of the outer article to secure the first substantially liquid impervious barrier panel and the medial portion of the outer article together, and the junction of the second convex side edge of the second substantially liquid impervious barrier panel and the second concave side edge of the medial portion of the outer article to secure the second substantially liquid impervious barrier panel and the medial portion of the outer article together, wherein the first portion of the first substantially liquid impervious barrier panel overlaps only a portion of the medial portion of the outer article proximate to the first concave side edge, and the first portion of the second substantially liquid impervious barrier panel overlaps only a portion of the medial portion of the outer article proximate to the second concave side edge, such that a portion of the inner surface of the medial portion of the outer article extends between the first and second substantially liquid impervious barrier panels, and wherein the first linear side edge of the first substantially liquid impervious barrier panel comprises a first free edge that is spaced from the inner surface of the outer article in a direction extending from the outer surface toward the inner surface and extends between a first point of the first concave side edge of the medial portion of the outer article that is proximate to the first end thereof and a second point of the first concave side edge of the medial portion of the outer article that is proximate to the second end thereof, and the second linear side edge of the second substantially liquid impervious barrier panel comprises a second free edge that is spaced from the inner surface of the outer article in a direction extending from the outer surface toward the inner surface and extends between a first point of the second concave side edge of the medial portion of the outer article that is proximate to the first end thereof and a second point of the second concave side edge of the medial portion of the outer article that is proximate to the second end thereof.

2. The washable diaper of claim 1, wherein the at least one member is substantially liquid impervious.

3. The washable diaper of claim 1, wherein the at least one member is sewn over the junction of the first convex side edge of the first substantially liquid impervious barrier panel and the first concave side edge of the medial portion of the outer article, and over the junction of the second convex side edge of the second substantially liquid impervious barrier panel and the second concave side edge of the medial portion of the outer article.

4. The washable diaper of claim 3, wherein the at least one member is sewn with substantially non-wicking thread.

5. The washable diaper of claim 1, wherein the at least one member extends over an outer surface of the first portions of the first and second liquid impervious barrier panels, the first and second convex side edges of the first and second substantially liquid impervious barrier panels, respectively, the first and second concave side edges of the medial portion of the outer article, respectively, and the outer surface of the outer article.

6. The washable diaper of claim 5, wherein the at least one member is secured via thread, and wherein the thread extends through the portion of the at least one member that extends over the outer surface of the first portions of the first and second liquid impervious barrier panels proximate, the first portions of the first and second substantially liquid impervious barrier panels, the outer article, and the portion of the at least one member that extends over the outer surface of the outer article.

7. The washable diaper of claim 1, wherein at least one elasticized member is attached to each of the first and second linear side edges of the first and second substantially liquid impervious barrier panels, respectively.

8. The washable diaper of claim 1, wherein at least one of the first and second ends of the outer article includes a substantially liquid impervious compartment formed between first and second layers of substantially liquid impervious material.

9. The washable diaper of claim 1, further including an inner liner system comprising at least one washable article having a first end and a second end, wherein when the inner liner system is assembled with the outer article at least one of the first and second ends of the at least one washable article is positioned within the substantially liquid impervious compartment between the first and second layers of substantially liquid impervious material.

10. The washable diaper of claim 9, wherein when the inner liner system is assembled with the outer article and the washable diaper is worn by a user, the first layer of substantially liquid impervious material is positioned between the user and the at least one washable article.

11. The washable diaper of claim 1, wherein the first and second concave side edges of the medial portion of the outer article define a width of the medial portion of the outer article, and wherein the first and second concave side edges of the outer article are concave along the width of the medial portion and the first and second convex side edges of the first and second substantially liquid impervious barrier panels, respectively, are convex along the width of the medial portion.

12. The washable diaper of claim 1, wherein the first and second opposing concave side edges of the an outer article extend inwardly toward the interior of the medial portion of the outer article.

13. The washable diaper of claim 1, wherein the first and second opposing convex side edges of the first and second substantially liquid impervious barrier panels, respectively, extend outwardly away from the interior of the medial portion of the outer article.

* * * * *